(12) United States Patent
Eppler et al.

(10) Patent No.: US 10,695,273 B2
(45) Date of Patent: *Jun. 30, 2020

(54) COMPOSITIONS CONTAINING BIO-BASED FARNESENE OR COMPOUNDS DERIVED THEREFROM AND THEIR USE IN CONSUMER AND INDUSTRIAL PRODUCTS

(71) Applicant: AMYRIS, INC., Emeryville, CA (US)

(72) Inventors: Ross Eppler, Emeryville, CA (US); Diva Chan, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/765,455

(22) PCT Filed: Sep. 29, 2016

(86) PCT No.: PCT/US2016/054542
§ 371 (c)(1),
(2) Date: Apr. 2, 2018

(87) PCT Pub. No.: WO2017/059136
PCT Pub. Date: Apr. 6, 2017

(65) Prior Publication Data
US 2018/0289601 A1    Oct. 11, 2018

Related U.S. Application Data

(60) Provisional application No. 62/236,771, filed on Oct. 2, 2015.

(51) Int. Cl.
*A61K 8/31* (2006.01)
*A61K 8/37* (2006.01)
(Continued)

(52) U.S. Cl.
CPC .............. *A61K 8/31* (2013.01); *A61K 8/37* (2013.01); *A61Q 5/00* (2013.01); *A61Q 19/001* (2013.01); *A61Q 19/10* (2013.01); *A61K 2800/10* (2013.01)

(58) Field of Classification Search
None
See application file for complete search history.

(56) References Cited

U.S. PATENT DOCUMENTS

| 5,786,310 A | 7/1998 | Dubief et al. |
| 7,691,792 B1 | 4/2010 | Fisher et al. |

(Continued)

FOREIGN PATENT DOCUMENTS

| CA | 2862593 | 8/2015 |
| EA | 200801717 A1 | 2/2009 |

(Continued)

OTHER PUBLICATIONS www.businessdictionary.com/definition/consumer-product.html, obtained on Feb. 20, 2019 (Year: 2019).*

(Continued)

*Primary Examiner* — Robert A Wax
*Assistant Examiner* — Melissa S Mercier
(74) *Attorney, Agent, or Firm* — Squire Patton Boggs (US) LLP

(57) ABSTRACT

The present invention provides compositions and methods of using the compositions as personal care products and other consumer and industrial products, wherein the compositions comprise bio-based farnesene and/or compounds derived from the bio-based farnesene.

23 Claims, 1 Drawing Sheet

(51) Int. Cl.
*A61Q 19/10* (2006.01)
*A61Q 5/00* (2006.01)
*A61Q 19/00* (2006.01)

(56) References Cited

U.S. PATENT DOCUMENTS

| | | | |
|---|---|---|---|
| 8,519,204 B2 | 8/2013 | Ohler et al. | |
| 10,071,034 B2* | 9/2018 | Eppler | A61Q 5/00 |
| 2007/0166275 A1 | 7/2007 | Gan et al. | |
| 2009/0149361 A1 | 6/2009 | Adkison et al. | |
| 2011/0287988 A1* | 11/2011 | Fisher | C07C 9/22 508/110 |
| 2014/0148624 A1* | 5/2014 | Ohler | C07C 5/05 585/18 |
| 2015/0018563 A1* | 1/2015 | Tabor | A61Q 5/12 548/478 |
| 2017/0240832 A1* | 8/2017 | Hahn | C10M 101/02 |
| 2019/0054008 A1 | 2/2019 | Chan | |

FOREIGN PATENT DOCUMENTS

| | | | |
|---|---|---|---|
| EP | 0 007 076 | 1/1980 | |
| FR | 2 596 061 | 9/1987 | |
| JP | 2012233281 | 11/2012 | |
| RU | 2109038 C1 | 4/1998 | |
| WO | WO 2010/015487 A2 | 2/2010 | |
| WO | WO-2010015487 A2 * | 2/2010 | A61K 8/31 |
| WO | WO 2011/146837 A1 | 11/2011 | |
| WO | WO 2012/141783 A1 | 10/2012 | |
| WO | WO 2012/141784 A1 | 10/2012 | |

OTHER PUBLICATIONS

International Search report and written opinion dated Dec. 22, 2016 for PCT/US2016/054542, 10 pages.
International Search Report and Written Opinion dated Aug. 3, 2015 for PCT/US2015/028954; 13 pages.
International Search report and written opinion dated Jan. 12, 2017 for PCT/US2016/053111; 11 pages.
Database WPI, Thomson Scientific, London, AN 1993-224472, XP002741774; and JP H05 148499, Jun. 1993, abstract.
Farmer et al., "Rubber, Polyisoprene and Allied Compounds. Part I. The Synthesis of Low-Molecular Polyisoprenes of the Rubber and the Squalene Type", Journal of the Chemical Society, Chemical Society, Letchworth; Jan. 1942, pp. 116-121, XP008141093.
Potential impacts of synthetic biology on livelihoods and biodiversity: eight case studies on commodity replacement. A submission to the convention on biological diversity from ETC group, etc Group, Jul. 2013, pp. 1-27.
Runge, Wolfgang; Technology Entrepreneurship. A Treatise on Entrepreneurs and Entrepreneurship for and in Technology Ventures, 2014, vol. 2, pp. 1069, 1093, 1101.
Schneiderman et al., "Juvenile Hormone Activity of Structurally Unrelated Compounds", Journal of Insect Physiology, Jan. 1965, vol. 11, pp. 1641-1649.
Sigma-Aldrich (https://www.sigmaaldrich.com/catalog/product/aldrich/124249?lang=en&region=US, Accessed Dec. 5, 2017, pp. 1-3).
Squalane & Synthetic Biology. Saffron & Synthetic Biology—A Case Study, May 2014, pp. 1-2.

* cited by examiner

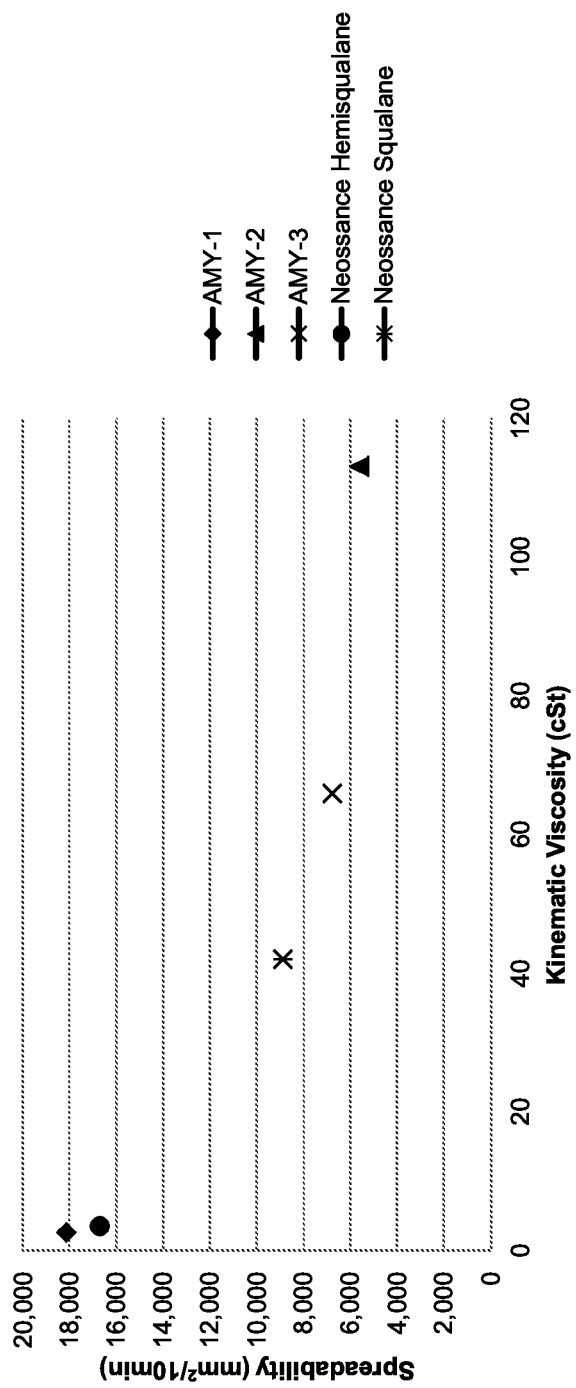

COMPOSITIONS CONTAINING BIO-BASED FARNESENE OR COMPOUNDS DERIVED THEREFROM AND THEIR USE IN CONSUMER AND INDUSTRIAL PRODUCTS

1. CROSS REFERENCE TO RELATED APPLICATION

This application is a U.S. national phase entry of International Patent Application No. PCT/US2016/054542, which claims benefit of priority to U.S. Provisional Patent Application No. 62/236,771, filed Oct. 2, 2015, which is incorporated herein by reference.

2. FIELD OF THE INVENTION

The present invention relates to compositions, methods and products containing bio-based farnesene or compounds derived therefrom and their use in consumer and industrial products.

3. BACKGROUND

Many personal care products, such as cosmetics, contain chemical materials that are derived from petroleum or extracted from plants. However, the use of these materials depletes natural resources and is not sustainable. Furthermore, petroleum derived oils such as mineral oil, when applied to the skin, are occlusive in nature. They can seal off the skin from air and water, and block the pores and the skins' natural respiration process. Blocked pores can result in trapped dirt and oil, leading to blackheads, pimples, and other undesirable skin conditions. The occlusive nature of petroleum derived oils can also create a warm, moist environment for bacteria or fungi to grow. Therefore, petroleum derived chemical materials are not ideal in personal care product formulations.

There is also a continuing need for new feedstock materials, preferably derived from renewable sources. In particular, many commercially available consumer and industrial products contain solvents that include volatile organic compounds (VOCs), which are environmentally unfriendly. Solvent compositions are useful in a wide range of products for removing organic and other substances of furniture, floors, walls, mechanical devices, automobiles, bicycles, clothing, skin and the like. Useful solvents have advantageous properties, such as vapor pressures, viscosities, degreasing powers, stabilities, odor and/or color. For many applications, advantageous safety profiles are desired. Solvent compositions with low environmental impact and low VOC content are needed, and few solvent compositions have been provided from sustainable, renewable sources.

Therefore, there is a need to develop alternative sources to the petroleum derived chemical materials and plant extracted compounds in personal care products. There is also a continuing need for new solvent compositions with desired properties, if possible, from sustainable, renewable sources. Embodiments of the present invention meet these and other needs.

4. SUMMARY

Provided herein are compositions, methods of making and using industrial and consumer products that are derived from bio-based chemical materials. As used herein, bio-based materials include compounds that are made by fermentation of renewable sources such as sugar, by microorganisms. The bio-based materials can be used directly in consumer and industrial products or can be derivatized (e.g., through catalytic, chemical and/or thermal reactions) prior to use. In one aspect, provided herein is a personal care product comprising bio-based farnesene, one or more hydrocarbon compounds derived from the bio-based farnesene, farnesene dimethyl maleate adduct, or a combination thereof, wherein the personal care product composition is formulated to be applied to skin, hair or nails.

In another aspect, provided herein is an industrial or consumer product composition comprising bio-based farnesene, one or more hydrocarbon compounds derived from bio-based farnesene, farnesene dimethyl maleate adduct, or a combination thereof, wherein the industrial or consumer product composition is formulated to be applied to a substrate for cleaning or degreasing.

In certain embodiments, the composition comprises bio-based farnesene. In certain embodiments, the composition comprises one or more hydrocarbons which are $C_{15}$ or $C_{30}$ hydrocarbons derived from bio-based farnesene. In certain embodiments, the composition comprises a partially hydrogenated farnesene derived from bio-based farnesene. In certain embodiments, the composition comprises dihydrofarnesene derived from bio-based farnesene. In certain embodiments, the composition comprises dihydrofarnesene and tetrahydrofarnesene derived from bio-based farnesene. In certain embodiments, the composition comprises about 78 wt. % to about 97 wt. % dihydrofarnesene and about 2 wt. % to about 20 wt. % tetrahydrofarnesene, compared to a total amount of farnesene and farnesene derivatives in the composition. In certain embodiments, the composition comprises farnesane derived from bio-based farnesene. In certain embodiments, the composition comprises squalane derived from bio-based farnesene. In certain embodiments, the composition comprises squalane and isosqualane derived from bio-based farnesene. In certain embodiments, the composition comprises squalane, isosqualane, and neosqualane derived from bio-based farnesene. In certain embodiments, the composition comprises farnesene dimer derived from bio-based farnesene. In certain embodiments, the composition comprises farnesane dimer derived from bio-based farnesene. In certain embodiments, the composition comprises farnesene dimethyl maleate adduct derived from bio-based farnesene and dimethyl maleate. In certain embodiments, the composition further comprises water, emulsifier, emollient, flavor, fragrance, essential oil, or a combination thereof.

In certain embodiments, the personal care product compositions are formulated as a hair care product, lip care product, skin care product, hygiene product, body care product, cosmetic makeup, or sun care product. In certain embodiments, the personal care product compositions are formulated as shampoo, conditioner, anti-frizz treatment, hair repair serum, lip gloss, lip balm, face serum, face cream, night cream, eye serum, eye cream, moisturizer, makeup remover, face cleanser, sanitizing lotion, body lotion, after shave lotion, or sun block lotion.

In certain embodiments, the consumer or industrial product compositions are formulated as cleanser, degreaser, metal cleaner, solvent, and other end uses. In certain embodiments, the consumer or industrial compositions are formulated as hard surface heavy duty cleaners, hand cleaners, graffiti removers, crayon/pen ink removers, bug and tar removers, engine degreasers, laundry pre-spotters, oven cleaners, auto interior cleaners, all-purpose cleaner concentrates, metal cleaning fluids, adhesive removers or paint strippers.

5. BRIEF DESCRIPTION OF THE FIGURE

FIG. 1 illustrates kinematic viscosity and spreadability of bio-based farnesene derived compounds in a graph.

6. DETAILED DESCRIPTION OF THE EMBODIMENTS

6.1 Definitions

When referring to the compounds, compositions and methods provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

As used herein, the term "bio-based farnesene" refer to farnesene which is biologically produced from microorganisms, in particular, genetically modified microorganisms, by fermentation of renewable carbon sources such as sugar.

As used herein, the term "a hydrocarbon compound derived from bio-based farnesene" refers to a compound comprising organic material consisting of carbon and hydrogen, which is produced from bio-based farnesene by catalytic reaction, chemical reaction, thermal reaction, hydrogenation, or any combination thereof.

"Farnesene" as used herein refers to α-farnesene, β-farnesene or a mixture thereof "α-farnesene" refers to a compound having the following structure:

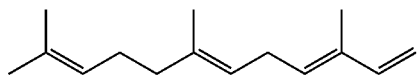

stereoisomer or a mixture of stereoisomers thereof.

"β-farnesene" refers to a compound having the following structure:

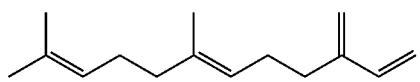

stereoisomer or a mixture of stereoisomers thereof. In some variations, β-farnesene comprises a substantially pure stereoisomer of β-farnesene. In other variations, β-farnesene comprises a mixture of stereoisomers, such as cis-trans isomers. In further embodiments, the amount of each of the stereoisomers in the β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the β-farnesene mixture, where wt. % is percent (%) by weight.

"Farnesane" refers to a compound having the following structure:

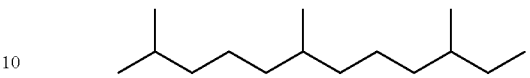

stereoisomer or a mixture of stereoisomers thereof.

"Hydrogenated farnesene" refers to farnesene (e.g., β-farnesene) wherein at least one carbon-carbon double bond is hydrogenated. Hydrogenated farnesene encompasses, for example, β-farnesene in which one, two, three or four double bonds are hydrogenated. Hydrogenated farnesene is obtained by complete or partial hydrogenation of farnesene, and encompasses farnesane.

"Partially hydrogenated farnesene" refers to farnesene (e.g., β-farnesene) wherein one, two, or three double bonds are hydrogenated. Partially hydrogenated farnesene can be obtained by partial hydrogenation of farnesene. In some embodiments, a composition comprising partially hydrogenated farnesene (e.g., obtained by partial hydrogenation of farnesene) may include amounts of farnesene and/or farnesane in addition to one or more of dihydrofarnesene, tetrahydrofarnesene and hexahydrofarnesene.

As used herein, the term "dihydrofarnesene" refers to farnesene in which one double bond is hydrogenated.

As used herein, the term "tetrahydrofarnesene" refers to farnesene in which two double bonds are hydrogenated.

As used herein, the term "hexahydrofarnesene" refers to farnesene in which three double bonds are hydrogenated.

"Total farnesene/farnesane" refers to the total amount of farnesene and farnesene derivative molecules in a composition. Farnesene derivatives include dihydrofarnesene, tetrahydrofarnesene, hexahydrofarnesene, and farnesane, and multimers thereof, as well as multimers of farnesene. Farnesene derivatives can further include reactive derivatives of farnesene and/or farnesane. These include oxidative derivatives, hydroxyl derivatives such as farnesol, epoxy derivatives, and other derivatives of farnesene and/or farnesane recognized by those skilled in the art. In some embodiments, a composition comprising partially hydrogenated farnesene (also referred to as "a partially hydrogenated farnesene composition") comprises farnesene and farnesene derivatives.

As used herein, "squalane" refers to a compound having the following formula:

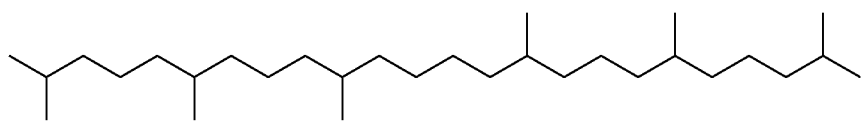 [SMILES: CC(C)CCCC(C)CCCC(C)CCCCC(C)CCCC(C)CCCC(C)C]

stereoisomer or a mixture of stereoisomers thereof.

As used herein, "iso-squalane" or "isosqualane" refers to a compound having the following formula:

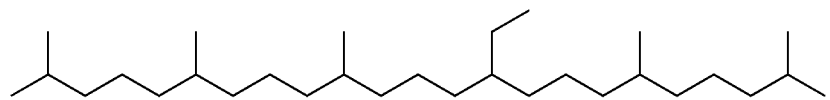 [SMILES: CCC(CCCC(C)CCCC(C)C)CCCC(C)CCCC(C)CCCC(C)C]

stereoisomer or a mixture of stereoisomers thereof.

As used herein, "neosqualane" refers to a compound having the following formula:

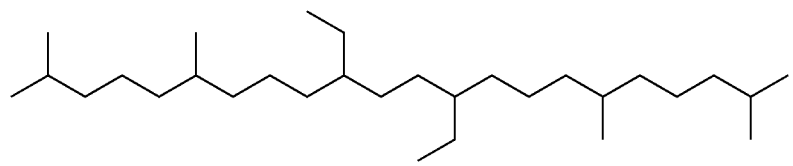 [SMILES: CCC(CCCC(C)CCCC(C)C)CCC(CC)CCCC(C)CCCC(C)C]

stereoisomer or a mixture of stereoisomers thereof.

As used herein, the term "farnesene dimer" refers to compounds having the following formula:

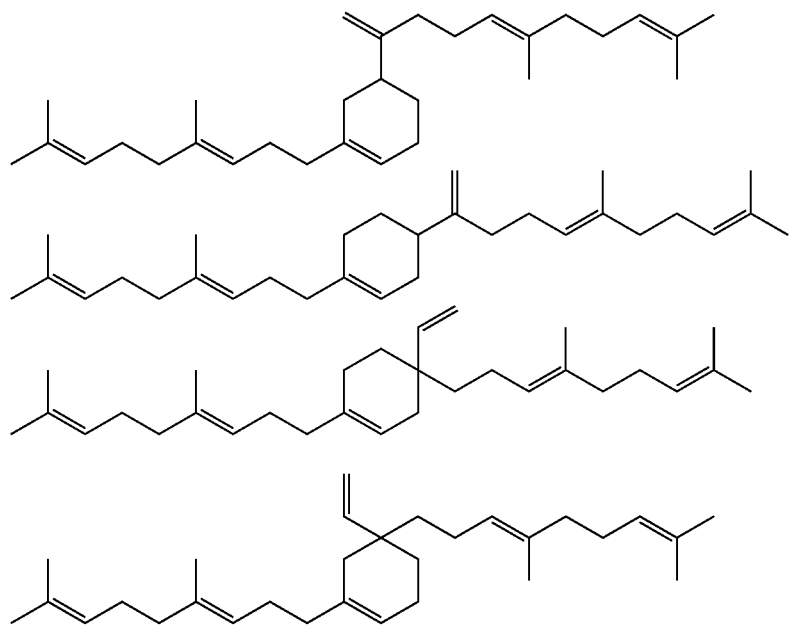

stereoisomers or a mixture of stereoisomers thereof.

As used herein, the term "farnesane dimer" refers to compounds having the following formula:

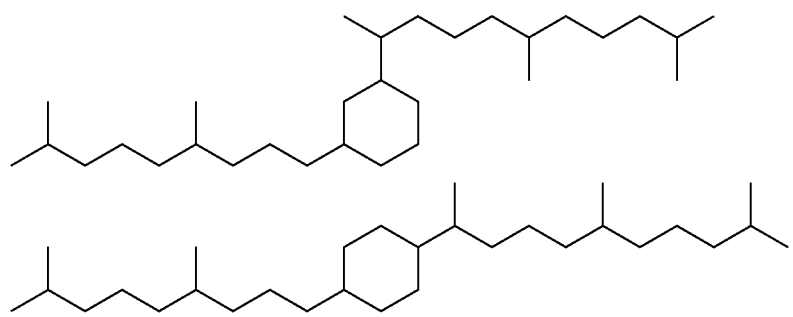

-continued

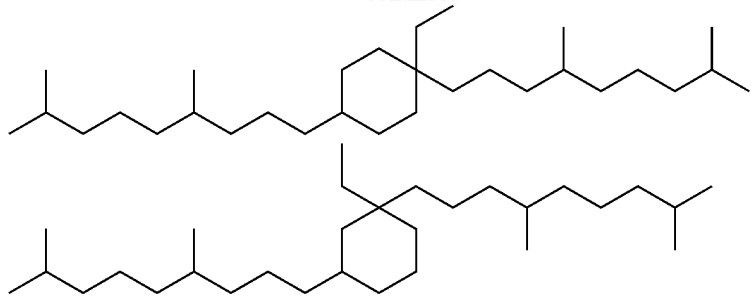

stereoisomers or a mixture of stereoisomers thereof.

As used herein, the term "farnesene dimethyl maleate adduct" refers to a compound having the following formula, a stereoisomer or a mixture of stereoisomers thereof:

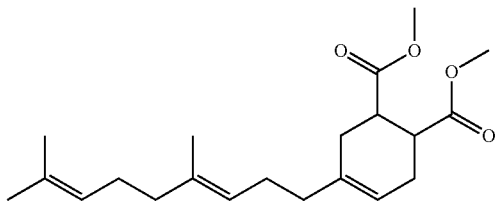 [SMILES: COC(=O)C1CC=C(CC/C=C(\C)CCC=C(C)C)CC1C(=O)OC]

As used herein, % with reference to hydrocarbon compositions refers to % measured as wt. % or as area % by GC-MS or GC-FID, unless specifically indicated otherwise.

The term "substantially free of" or "substantially in the absence of," when used in connection with an article (including, but not limited to, a compound or composition comprising a compound), refers to the article that includes at least 85% or 90% by weight, in certain embodiments, 95%, 98%, 99%, or 100% by weight, of the designated article.

In the following description, all numbers disclosed herein are approximate values, regardless of whether the word "about" or "approximate" is used in connection therewith. Numbers may vary by 1%, 2%, 5%, or by 10 to 20%. Whenever a numerical range with a lower limit $R^L$ and an upper limit $R^U$ is disclosed, any number falling within the range is specifically disclosed. In particular, the following numbers $R_k$ within the range are specifically disclosed: $R_k = R^L + k*(R^U - R^L)$, wherein k is a variable ranging from 0.01 to 1 with a 0.01 increment, i.e., k is 0.01, 0.02, 0.03, 0.04, 0.05, . . . , 0.5, 0.51, 0.52, . . . , 0.95, 0.96, 0.97, 0.98, 0.99, or 1. Further, any numerical range defined by any two numbers $R_k$ as defined above is also specifically disclosed herein.

The term "renewable carbon" source refers to a carbon source that is made from modern carbon that can be regenerated within a several months, years or decades rather than a carbon source derived from fossil fuels (e.g., petroleum) that takes typically a million years or more to regenerate. The terms "renewable carbon" and "bio-based carbon" are used interchangeably herein. "Atmospheric carbon" refers to carbon atoms from carbon dioxide molecules that have been free in earth's atmosphere recently, e.g., in the most recent few decades. For example, bio-based farnesene used in any one of the embodiments described herein can be made from microorganisms, including bioengineered microorganisms, using a renewable carbon source.

The term "a," "an," and "the" means "at least one" unless the context clearly indicates otherwise. Use of the plural herein includes the singular unless the context clearly indicates otherwise. For example "articles" would refer to one article as well as two or more articles unless the context clearly indicates otherwise.

6.2 Bio-Based Farnesene, Hydrocarbon Compounds Derived from Bio-Based Farnesene and Farnesene Dimethyl Maleate Adduct In another aspect of the invention, provided herein are compounds that are useful in producing personal care product compositions and a wide variety of consumer and industrial product compositions. In certain embodiments, bio-based farnesene, which is produced by fermentation of renewable carbon sources, is used in these compositions. In other embodiments, the bio-based farnesene is further processed, for example catalytically, chemically and/or thermally, to produce other compounds useful in formulations for personal care and other products. In certain embodiments, bio-based farnesene and other compounds derived from the bio-based farnesene are further processed so that they are free or substantially free of impurities. For example, a composition comprising one or more compounds derived from bio-based farnesene provided herein is free or substantially free of small, volatile, organic oxygenate compounds (e.g., alcohols, acids, aldehydes, 6-methyl-5-penten-2-one, or the like) which can cause an odor in consumer or industrial product compositions.

6.2.1. Bio-Based Farnesene

In certain embodiments, bio-based farnesene is produced from microorganisms, including bioengineered microorganisms, using a renewable carbon source such as sugar. Because bio-based farnesene can be made by fermentation of organic compounds such as sugar by microorganisms, the bio-based farnesene is useful in making eco-friendly chemical compounds which can be used for various consumer and industrial product compositions.

In particular embodiments, bio-based farnesene can be produced from fermentation of renewable carbon sources such as sugar using genetically modified microorganisms. In some embodiments, the microorganisms are genetically modified microorganisms in which nucleic acid molecules have been inserted, deleted or modified to produce bio-based farnesene. The methods for producing bio-based farnesene using microorganisms are described in, e.g., U.S. Pat. No. 7,659,097 B2, U.S. Pat. No. 7,399,323 B2, U.S. Pat. No. 7,846,222 B2, U.S. Pat. No. 8,257,957 B2 or International Patent Publication WO2007/139924 A2, each of which is incorporated herein by reference in its entirety.

6.2.2. $C_{15}$ Hydrocarbon Compounds Derived from Bio-Based Farnesene

Bio-based farnesene derived from fermentation of renewable carbons can be used to generate additional $C_{15}$ hydrocarbon compounds which are also suitable in formulations in a variety of consumer or industrial products. For example, bio-based farnesene can be hydrogenated to produce farnesane or partially hydrogenated farnesene. Farnesane is the fully hydrogenated $C_{15}$ compound of farnesene. Partially hydrogenated $C_{15}$ compounds include dihydrofarnesene, where one double bond of farnesene is hydrogenated. During partial hydrogenation process, other partially hydrogenated farnesenes, such as tetrahydrofarnesene and hexahydrofarnesene, may be co-produced with dihydrofarnesene. Any one or combinations of $C_{15}$ hydrocarbon compounds derived from bio-based farnesene may be used in formulations for consumer or industrial products.

Generally, the production of other $C_{15}$ hydrocarbon compositions using bio-based farnesene as substrates comprises reacting a controlled amount of hydrogen with the bio-based farnesene in the presence of a catalyst under controlled reaction conditions. Any suitable hydrogenation catalyst may be used. For example, in some variations, a catalyst is selected from the group consisting of Pd, Pt, Ni, Ru, Ir, Cu, Fe, Raney-type porous catalysts such as Ni/Al, Co/Al and Cu/Al, alloys of platinum group catalysts with promoters or stabilizers such as Mo, Co, Mg and Zn, and hydroprocessing catalysts such as NiMoS and CoMoS. Exemplary catalysts are described in U.S. Pat. Nos. 6,403,844; 5,378,767; 5,151,172; and 3,702,348, each of which is incorporated herein by reference in its entirety. In certain embodiments, the controlled amount of hydrogen corresponds to a molar equivalent of desired degree of hydrogenation in the bio-based farnesene. For example, to produce a 75% hydrogenated farnesene from bio-based farnesene, the controlled amount of hydrogen would be about 3 molar equivalents of hydrogen. Any suitable configuration for staged partial hydrogenation may be used to carry out the reaction with various catalyst conditions (e.g., structure of catalyst, type of catalyst, catalyst loading, reaction time, temperature and/or hydrogen pressure). For example, hydrogenations can be carried out in stages, a first stage, a second stage, and subsequence stages, if desired. The catalytic and hydrogenation conditions may be independently varied to produce partially hydrogenated farnesenes with a different degree of hydrogenation.

In certain embodiments, a mixture of compounds derived from bio-based farnesene comprises at least about 70% of dihydrofarnesene, compared to the total amount of $C_{15}$ hydrocarbons present in the mixture. In certain embodiments, the mixture of compounds may comprise at least about 75%, at least about 80%, at least about 85%, at least about 90%, or at least about 95% dihydrofarnesene, compared to the total amount of $C_{15}$ hydrocarbons present in the mixture. In certain embodiments, the mixture of compounds comprises, on average, about 1.0 to about 1.25 double bonds per molecule of farnesene and farnesene derivatives in the mixture. The mixture of compounds comprising a relatively high proportion of dihydrofarnesene is particularly useful as a solvent.

The detailed description for producing farnesene, farnesane, and partially hydrogenated farnesene can be found in PCT Application Publication Nos. WO2012/141783 and WO2012/141784, which are incorporated herein by reference in their entirety. Additional description for producing partially hydrogenated farnesenes can be found in U.S. Patent Application Publication No. 2015/0315520, which is incorporated herein by reference in its entirety. Bio-based farnesene is also commercially available and can be purchased from Amyris Inc. (Emeryville, Calif.). Farnesane and partially hydrogenated farnesene are also commercially available as, for example, Neossance® Hemisqualane and Myralene™ 10 Fluid, respectively, from Amyris Inc. (Emeryville, Calif.).

6.2.3. $C_{30}$ Hydrocarbon Compounds Derived from Bio-Based Farnesene

The bio-based farnesene derived from fermentation of renewable carbons can be used to generate $C_{30}$ hydrocarbon compounds which are also suitable in formulations for various consumer and industrial products. Examples of $C_{30}$ hydrocarbons derivable from bio-based farnesene include squalane, farnesene dimers, and farnesane dimers. In certain embodiments, bio-based farnesene is chemically dimerized and then hydrogenated to produce squalane. The squalene composition provided herein can be differentiated from squalanes derived from shark oils or olive oils by the presence of isosqualane, which is co-produced with squalane from the catalytic reaction of bio-based farnesene as a substrate and subsequent hydrogenation process. In certain embodiments, neosqualane and isosqualane are co-produced with squalane. In certain embodiments, the squalane composition derived from bio-based farnesene contains fewer impurities and/or lower quantities of impurities compared to squalanes obtained from olive pits or other phyto-squalanes.

Any suitable catalysts may be used for the catalytic reaction to produce squalane and other $C_{30}$ hydrocarbons from bio-based farnesene. In certain embodiments, preformed or in situ-generated palladium catalysts can be used to catalyze the dimerization of bio-based farnesene to form a reaction product comprising isosqualene and structural isomers of isosqualene, and the reaction product or at least a portion of the reaction product can be hydrogenated to form a composition comprising squalane and isosqualane, and in some variations, also neosqualane. In contrast to a squalene composition derived from bio-based farnesene, squalene oils derived from olives or from shark liver do not comprise isosqualane.

In certain embodiments, palladium catalysts can be used to catalyze the dimerization of bio-based farnesene. In certain embodiments, the catalyst used herein is formed from a palladium precursor selected from $[Pd(allyl)Cl]_2$, $Pd(cod)Cl_2$, $[Pd(allyl)Cl]_2$, $Pd(cod)Cl_2$, $Pd_2(dba)_3$, $Pd(dba)_2$, $Pd(dba)$, $Pd(acac)_2$, or an equimolar mixture of $Pd(dba)_3$ and $Pd_2(dba)_3$. In certain embodiments, the resulting catalyst comprises a phosphine ligand. In certain embodiments, the phosphine ligand is selected from triphenyl phosphine, triethyl phosphine and tritolyl phosphine.

In certain embodiments, dimerization of bio-based farnesene produces isosqualene, which can be subsequently hydrogenated to produce $C_{30}$ hydrocarbon compositions. In certain embodiments, the hydrogenation reaction can be carried out in the presence of hydrogen with a catalyst such as Pd, Pd/C, Pt, $PtO_2$, $Ru(PPh_3)_3Cl_2$, $Rh(PPh_3)_3$, Ru/C, Raney nickel, nickel, or combinations thereof. The hydrogenation reaction can be carried out as known to one of skill in the art, as reported in PCT Application Publication No. WO 2010/044208, which is incorporated herein by reference in its entirety.

Hydrogenated dimerization products resulting from these catalyst systems may be hydrocarbon compositions comprising squalane and isosqualane, wherein a ratio of (quantity by weight squalane):(quantity by weight isosqualane) is in a range from about 2:1 to about 26:1, e.g., 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1 or 26:1. In certain embodiments, the ratio of (quantity by weight squalane):(quantity by weight isosqualane) is in a range from about 2:1 to about 25:1, from about 2:1 to about 20:1, from about 3:1 to about 20:1, from about 5:1 to about 15:1, or from about 2:1 to about 10:1. In certain embodiments, hydrocarbon compositions comprising squalane and isosqualane can be a carrier medium. In certain embodiments, the carrier medium consists of a $C_{30}$ hydrocarbon composition (e.g., a squalane composition), obtained from bio-based farnesene, comprising at least about 85% by weight of squalane and equal to or less than about 15% by weight of isosqualane, based on the total weight of the $C_{30}$ hydrocarbon composition. In certain embodiments, the carrier medium consists of a $C_{30}$ hydrocarbon composition comprising at least about 90% by weight of squalane and equal to or less than about 10% by weight of isosqualane, based on the total weight of the $C_{30}$ hydrocarbon composition. In certain embodiments, the carrier medium consists of a $C_{30}$ hydrocarbon composition comprising from about 90% to about 98% by weight of squalane and from about 2% to about 10% by weight of isosqualane, based on the total weight of the $C_{30}$ hydrocarbon composition.

Other suitable catalysts may be used if it is desired to produce squalane compositions comprising different proportions of squalane and isosqualane. For example, zirconium, titanium or hafnium catalysts can be used to catalyze the dimerization of bio-based farnesene to produce a reaction product, which, when hydrogenated, comprises isosqualane as the predominate product of squalane and isosqualane. The additional details about the catalysts, catalytic reactions and hydrogenation conditions are described in PCT Application Publication No. WO2011/146837, which is incorporated herein by reference in its entirety.

In another aspect, farnesene dimers and farnesane dimers may be added to the present formulations for consumer and industrial products. The farnesene dimers may be derived from bio-based farnesene using any suitable methods. For example, bio-based farnesene may be heated to 220° C. and stirred to produce farnesene dimers. The farnesane dimers may be produced by reducing farnesene dimers in the presence of hydrogen with a catalyst such as Pd, Pd/C, Pt, $PtO_2$, $Ru(PPh_3)_2Cl_2$, Raney nickel, or combinations thereof. The detailed description for producing hydrocarbon compositions comprising farnesene dimers and/or farnesane dimers can be found in U.S. Pat. Nos. 7,592,295, 7,691,792, and 8,669,403, which are incorporated herein by reference in their entirety. The squalane derived from bio-based farnesene is also commercially available as Neossance® squalane from Amyris, Inc. (Emeryville, Calif.). The farnesene dimer and farnesane dimers are also commercially available from Amyris, Inc. (Emeryville, Calif.).

6.2.4. Farnesene Dimethyl Maleate Adduct

Bio-based farnesene derived from fermentation of renewable carbons can be used to farnesene dimethyl maleate adduct which is suitable in formulations to produce a wide variety of consumer or industrial products. Any suitable process can be used to make farnesene dimethyl maleate adducts from bio-based farnesene. Typically, farnesene dimethyl maleate adducts are formed from Diels-Alder reactions of bio-based farnesene and dimethyl maleate. Generally, dimethyl maleate is charged into a reaction vessel. BHT is also charged into the reactor vessel. The reactor content is stirred and heated (e.g., to about 140+/−5° C.). Bio-based farnesene can then be charged into the reactor using a feed pump. The feed rate of bio-based farnesene is controlled to favor the Diels-Alder reaction over the formation of thermal dimers. Reactor contents are maintained for a suitable amount of time typically until GC-FID indicates reaction completion (e.g., approximately 20 hours). When the amount of dimethyl maleate remaining in the reactor is about 2 area % or less by GC-FID, temperature can be increased to 160° C. Optionally, additional BHT may be added to the reaction to control formation of high boiling side products. Optionally, the reaction products may be distilled to isolate the farnesene dimethyl maleate adduct from any residual reactants and higher boiling byproducts that may have been formed. Additional detail of Diels-Alders reactions of farnesene and dimethyl maleate can be found in, e.g., WO2013/028289 and WO2013/028290, which are herein incorporated herein by reference in their entirety.

6.3 Compositions for Personal Care Products and Other Consumer and Industrial Products and Methods of Use In certain embodiments, provided herein are compositions for personal care products and other consumer and industrial products. Bio-based farnesene and compounds derived therefrom (e.g., partially hydrogenated farnesene, farnesane, squalane, farnesene dimer, farnesane dimer, and farnesene dimethyl maleate adduct) possess many advantageous properties such as solvencies, emollience, spreadability, and/or viscosity. Due to their advantageous properties, the compositions provided herein can be used as a wide range of industrial or consumer products, such as solvents, cleaning products, degreasers, metal cleaners, and other end uses. For example, the compositions are fully compatible to be formulated in hard surface heavy duty cleaners, hand cleaners, graffiti removers, crayon/pen ink removers, bug and tar removers, engine degreasers, laundry pre-spotters, oven cleaners, auto interior cleaners, all-purpose cleaner concentrates and metal cleaning fluids, adhesive removers and paint strippers.

In addition, the compositions are also compatible to be formulated in a wide range of personal care products, such as hair care products (e.g., shampoo, conditioner, anti-frizz treatment, hair repair serum, and the like), lip care products (e.g., lip gloss, lip balm, and the like), skin care products (face serum, face cream, night cream, eye serum, eye cream, moisturizer, and the like), hygiene products (e.g., makeup remover, face cleanser, sanitizing lotion, nail polish remover, and the like), body care products (e.g., body lotion, after shave lotion, and the like), cosmetic makeup products, and sun care products (e.g., sun block lotion, sun tan lotion, and the like).

In certain embodiments, the compositions useful as industrial or consumer products (including personal care products) consist essentially of bio-based farnesene and/or compounds derived therefrom. In other embodiments, the compositions further comprise one or more additional components to produce end products such as a solvent, a degreaser, a general cleaning product, a metal cleaning product, a personal care product, and the like. In certain embodiments, the compositions further comprise one or more co-solvents or surfactants, or both. In certain embodiments, the compositions further comprise at least one additional component, such as a co-solvent, surfactant, water, emulsifier, emollient, thickener, or a mixture thereof.

In certain embodiments, the composition can further comprise additives known to the practitioner of skill in the art. Useful additives include, but are not limited to, delaminates, buffering agents, pH control agents, fragrances, perfumes, flavors, essential oils, defoamers, dyes, whiteners, brighteners, solubilizing materials, stabilizers, thickeners, corrosion inhibitors, lotions, mineral oils, enzymes, cloud point modifiers, preservatives, ion exchangers, chelating agents, sudsing control agents, soil removal agents, softening agents, opacifiers, inert diluents, graying inhibitors, stabilizers, polymers, abrasive, exfoliant, and the like, and combinations thereof.

In certain embodiments, one or more additional components/additives incorporated into the present compositions enhance properties or functions of end products. As used herein, the term additional component/additives do not include reactants or reaction products produced by catalytic or hydrogenation reactions of bio-based farnesene. One or more additional components/additives refer to components/additives deliberately added to the compositions for functional purposes. As used herein, the terms "component" and "additive" are used interchangeably, and the same ingredient, e.g., a limonene, may be referred to as a component (e.g., co-solvent) or an additive (e.g., fragrance) depending on its purpose and/amount in the composition.

In certain embodiments, useful co-solvents that can be added to the present compositions include, but are not limited to, saturated hydrocarbon solvents, glycol ethers, fatty acid methyl esters, aliphatic hydrocarbon solvents, acyclic hydrocarbon solvents, halogenated solvents, aromatic hydrocarbon solvents, cyclic terpenes, unsaturated hydrocarbon solvents, halocarbon solvents, polyols, ethers, glycol esters, alcohols, ketones, and any combination thereof. In an embodiment, a composition provided herein further comprises a co-solvent selected from the group consisting of limonene, benzene, toluene, xylene, aromatic high flash aromatic naptha (e.g., aromatic 200), soy methyl ester, ethyl lactate, paraffins (e.g., isopar M), dibasic esters (e.g., DBE-LVP), paraffinic naphthenic solvent, propylene glycol, ethyl alcohol, and mixtures thereof. The addition of such a co-solvent can cause the solvent blend-to-surfactant ratio in the composition to increase. Co-solvents can be used individually or in combination.

In certain embodiments, useful surfactants that can be added to the present compositions include, but are not limited to, nonionic surfactants, cationic surfactants, anionic surfactants, amphoteric surfactants, zwitterionic surfactants, and mixtures thereof. Examples of nonionic surfactants include, but are not limited to, one or more of amides such as alkanolamides, ethoxylated alkanolamides, ethylene bisamides; esters such as fatty acid esters, glycerol esters, ethoxylated fatty acid esters, sorbitan esters, ethoxylated sorbitan; ethoxylates such as alkylphenol ethoxylates, alcohol ethoxylates, tristyrylphenol ethoxylates, mercaptan ethoxylates; end-capped and EO/PO block copolymers such as ethylene oxide/propylene oxide block copolymers, chlorine capped ethoxylates, tetra-functional block copolymers; amine oxides such lauramine oxide, cocamine oxide, stearamine oxide, stearamidopropylamine oxide, palmitamidopropylamine oxide, decylamine oxide; fatty alcohols such as decyl alcohol, lauryl alcohol, tridecyl alcohol, myristyl alcohol, cetyl alcohol, ethyl alcohol, stearyl alcohol, oleyl alcohol, linoleyl alcohol and linolenyl alcohol; and alkoxylated alcohols such as ethoxylated lauryl alcohol, trideceth alcohols; and fatty acids such as lauric acid, oleic acid, stearic acid, myristic acid, cetearic acid, isostearic acid, linoleic acid, linolenic acid, ricinoleic acid, elaidic acid, arichidonic acid, myristoleic acid; and mixtures thereof. Other examples of non-ionic surfactants include a glycol such as polyethylene glycol (PEG), alkyl PEG esters, polypropylene glycol (PPG) and derivatives thereof. In one embodiment, the surfactant is an alcohol ethoxylate, an alkyl phenol ethoxylate or a terpene alkoxylate.

Examples of cationic surfactants include, but are not limited to, quaternary ammonium compounds, such as cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quatemium-13), stearyl dimethyl distearyldimonium chloride, dicetyl dimonium chloride, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, dicetyl dimonium chloride and distearyldimonium chloride; isostearylaminopropalkonium chloride and olealkonium chloride; behentrimonium chloride; as well as mixtures thereof.

Examples of anionic surfactants include, but are not limited to, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, sulfosuccinates, isethionates, and taurates, as well as mixtures thereof. Commonly used anionic surfactants that are suitable as the anionic surfactant component of the composition of the present invention include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium-monoalkyl phosphates, sodium dialkyl phosphates, sodium lauroyl sarcosinate, lauroyl sarcosine, cocoyl sarcosine, ammonium cocyl sulfate, ammonium lauryl sulfate, sodium cocyl sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium lauryl sulfate, potassium cocyl sulfate, potassium lauryl sulfate, monoethanolamine cocyl sulfate, sodium tridecyl benzene sulfonate, and sodium dodecyl benzene sulfonate. Branched anionic surfactants are particularly preferred, such as sodium trideceth sulfate, sodium tridecyl sulfate, ammonium trideceth sulfate, ammonium tridecyl sulfate, and sodium trideceth carboxylate.

Examples of amphoteric surfactants include, but are not limited to, derivatives of aliphatic secondary and tertiary amines in which the aliphatic radical can be straight chain or branched and wherein one of the aliphatic substituents contains from about 8 to about 18 carbon atoms and one contains an anionic water solubilizing group. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl arnphoglycinates, and alkyl amphopropionates, as well as alkyl iminopropionates, alkyl iminodipropionates, and alkyl amphopropylsulfonates, such as for example, cocoamphoacetate cocoarnphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

Examples of zwitterionic surfactants include, but are not limited to, alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

In certain embodiments, the compositions provided herein comprise surfactants such as sodium lauryl ether sulfate, ethoxylated alcohol surfactants (e.g., Tomadol 25-3, Tomadol 25-7), fatty acid diethanolamine (e.g., cocamide DEA), orange oil emulsifier (e.g., Videt ME-80), acrylate-based emulsion copolymer (e.g., Alcogum SL-70), polyoxyethers of lauryl alcohol (e.g., Laureth-7), linear isopropylamine dodecylbenzene sulfonate (e.g., Rhodocal IPAM), blended alcohol ethoxylate (e.g., Videt Q3), alkoxylated alcohol (e.g., Tergitol 15-S-7), sodium iminodipropionate (e.g., Amphoteric 400), nonionic alcohol ethoxylates (e.g., Ecosurf EH-6), a palm kernel alcohol ethoxylated and propoxylated surfactant (e.g., Ecosurf SA-7), sodium xylene sulfonate (e.g., Alkatrope SXS-40), or mixtures thereof.

In certain embodiments, useful emulsifiers that can be added to the present compositions include, but are not limited to, polysaccharide ethers, polyglycosides, fatty acids, fatty alcohols, amine oxides, water-soluble cellulose derivatives, alkyl sulfonates, ethoxylated alkyl phenols, alkanaolamides, betaines, zwiterionics, carboxylated alcohols, carboxylic acids, ethoxylated alcohols, and derivatives thereof. In certain embodiments, a composition provided herein further comprises emulsifiers, such as lauryl alcohol (e.g., Laureth-7), fatty acid diethanolamine (e.g., cocamide DEA), ammonium methyl sulfate and fatty alcohol ethoxylate (e.g., Steposol DG), Tomadyne 100 surfactant, linear alcohol (C12-15) ethoxylate, POE-7 (where POE is polyoxyethylene), POE-3, sodium branched dodecyl benzene sulfonate, or mixtures thereof.

In certain embodiments, useful emollients that can be added to the present compositions include, but are not limited to, conventional lipids materials (e.g., fats, waxes), polar lipids (lipids that have been modified to be more water soluble), silicones, hydrocarbons, and other solvent materials. Emollients can include, for example, petroleum based, fatty acid type, alkyl ethoxylate type, fatty acid ester ethoxylates, fatty alcohol type, polysiloxane type, mucopolysaccharides, or mixtures thereof. Other useful emollients also include polyhydric alcohols, e.g., glycerin and propylene glycol, and the like; polyols such as polyethylene glycols; saccharides and/or polysaccharides, such as sucrose, sorbitol; and urea derivatives such as hydroxyethyl urea and the like. In certain embodiments, the composition provided herein further comprises emollients, such as Crodamol STS (e.g., PPG-3 benzyl ether myristate), Versagel ME-750 (e.g., hydrogenated polyisobutene, butyelen/ethylene/styrene copolymer, ethylene/propylene/styrene copolymer), Softisan 649 (e.g., bis-diglyceryl polyacyladipate-2, Crodamol PTIS (pentaerythrityl tetraisosterate), Super Sterol Ester (e.g., $C_{10-30}$ cholesterol/lanosterol esters), or mixtures thereof.

In certain embodiments, useful thickeners that can be added to the present compositions include, but are not limited to, organic thickeners and inorganic thickeners. Organic thickeners may include cellulosic thickeners and their derivatives, natural gums, acrylates, starches, stearates, and fatty acid alcohols. Inorganic thickeners may include clays and salts. Examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Examples of acrylates include potassium aluminum polyacrylate, sodium acrylate/vinyl alcohol copolymer, sodium polymethacrylate, and the like. Examples of starches include oat flour, potato starch, wheat flour, wheat starch, and the like. Examples of stearates include methoxy PEG-22/dodecyl glycol copolymer, PEG-2M, PEG-5M, and the like. Examples of fatty acid alcohols include caprylic alcohol, cetearyl alcohol, lauryl alcohol, oleyl alcohol, palm kernel alcohol, and the like. Some non-limiting examples of clays include bentonite, magnesium aluminum silicate, magnesium trisilicate, stearalkonium bentonite, trimethylamine magnesium aluminum silicate, and the like. Some non-limiting examples of salts include calcium chloride, sodium chloride, sodium sulfate, ammonium chloride, and the like. Some non-limiting examples of thickeners that may be used to thicken the non-aqueous portions of the composition include waxes such as candelilla wax, carnauba wax, beeswax, and the like, oils, vegetable oils and animal oils, and the like. In certain embodiments, the present compositions may further comprise thickeners, such as acrylates $C_{10-30}$ cross polymer, Kelzan ASX-T (e.g., xanthan gum), linear alcohol ethoxylate, $C_{12-14}$, and mixtures thereof.

In certain embodiments, useful hydrotropes that can be added in the present compositions include, but are not limited to, sodium and ammonium xylene sulfonates, sodium alkyl disulfonates, solvents, particularly alcoholic solvents, such as ethanol, isopropanol, ethoxy diglycol, glycols and polyhydroxy compounds such as propylene glycol, methyl propane, diol, butylene glycol, hexylene glycol, glycerin, dextrose, sorbitol, sucrose, fructose, other sugars, or mixtures thereof.

In certain embodiments, useful pH control agents and/or buffers that can be added to the present compositions include, but are not limited to, sodium hydroxide, potassium hydroxide, tetraethylammonium, sodium citrate, acetic acid, citric acid, hydrochloric acid, and the like. A pH control agent can be added in an amount as needed to keep the composition at a desired pH. Buffers, such as sodium metasilicate, pentahydrate, sodium bicarbonate can also be used to keep the composition at a desired pH. For example, a pH control agent may be added to keep the composition pH selected from about 1 to about 14 depending on the end use of the composition. For example, a composition for heavy duty industrial cleaning application can be formulated to have a pH of about 11 or about 13-14 with a pH control agent and/or buffer. Generally, a pH control agent and/or buffer is added in a small amount in the range of from about 0.1% to about 10%, typically in the range from about 0.5% to about 5%, based on the total weight of the composition.

Depending on end use or application, bio-based farnesene and/or compounds derived therefrom can be mixed at any suitable proportions with one or more additional components to produce a composition. In certain embodiments, bio-based farnesene (or a compound derived therefrom, or a mixture thereof) may be added as a major weight percent component and one or more additional components may be added to the mixture as a minor weight percent component based on the total weight of the composition. For example, a composition may comprise 69 wt. % of bio-based farnesene (or a compound derived from therefrom, or a mixture thereof) and 31 wt. % of at least one additional component (e.g., emulsifier and/or carrier). In certain embodiments, the present composition comprises at least 50, 55, 60, 65, 70, 75, 80, 85, 90, 95, 96, 97, 98, or 99 wt. % of bio-based farnesene or a compound derived therefrom or a mixture thereof based on the total weight of the composition and at least one additional component. In certain embodiments, the present composition comprises bio-based farnesene or a compound derived therefrom or a mixture thereof as a minor weight percent component. For example, the present composition comprises less than about 50, 45, 40, 35, 30, 25, 20, 15, 10, 5, 4, 3, 2, or 1 wt. % of bio-based farnesene or a compound derived therefrom or a mixture thereof and at least one additional component/additive. In certain embodiments, the present composition comprises bio-based farnesene or a compound derived therefrom or a mixture thereof in any suitable range selected anywhere between about 0.1 wt. % to about 99.9 wt. %, typically between about 0.5 wt. % to about 99.9 wt. %, and at least one additional component, based on the total weight of the composition.

In certain embodiments, the present composition comprises a co-solvent as an additional component in the mixture with bio-based farnesene or a compound derived therefrom or a mixture thereof. In certain embodiments, a co-solvent can be included in the composition as a major weight percent component of the composition. For example, the composition can comprise at least about 50, 55, 60, 65, 70, 75, 80, 85, 90, 95, 96, 97, 98, or 99 wt. % of co-solvent and bio-based farnesene and/or a compound derived therefrom as a minor component. In other embodiments, the present composition comprises a co-solvent as a minor component. For example, the present composition comprises less than about 50, 45, 40, 35, 30, 25, 20, 15, 10, 5, 4, 3, 2, or 1 wt. % of a co-solvent and any suitable amount of bio-based farnesene and/or a compound derived therefrom. In certain embodiments, the present composition comprises a co-solvent in any suitable range selected anywhere between about 0.1 wt. % to about 99.9 wt. %, typically between about 0.5 wt. % to about 99 wt. %, based on the total weight of the composition. The amount of co-solvent added to the composition depends on end use or application of the composition. For example, in making a solvent blend, bio-based farnesene (or a compound derived therefrom, or a mixture thereof) and co-solvent(s) may be mixed at a ratio of about 70:30, 90:10, 75:25, or any suitable ratios as shown in the Examples section.

In certain embodiments, the present composition comprises bio-based farnesene (or a compound derived therefrom, or a mixture thereof) and a surfactant as an additional component. In certain embodiments, one or more surfactants are included in the composition as a major weight percent component. For example, the present composition can comprise one or more surfactants as a major component (e.g., 50 wt. %) of the total weight of the composition. In certain embodiments, the present composition can comprise at least 50, 55, 60, 65, 70, 75, 80, 85, 90, 95, 96, 97, 98, or 99 wt. % of one or more surfactants as a major weight percent component and bio-based farnesene (or a compound derived therefrom, or a mixture thereof) as a minor weight percent component based on the total weight of the composition. In other embodiments, one or more surfactants are included in the composition as a minor weight percent component. For example, the present composition can comprise less than about 50, 45, 40, 35, 30, 25, 20, 15, 10, 5, 4, 3, 2, or 1 wt. % of surfactant and any suitable amount of bio-based farnesene or a compound derived therefrom or a mixture thereof. In certain embodiments, the present composition comprises a surfactant in any suitable range selected anywhere between about 0.1 wt. % to about 99.9 wt. %, typically between about 0.5 wt. % to about 99 wt. %, based on the total weight of the composition. The amount of surfactant added to the present composition depends on end use or application of the composition. For example, about 6 wt. % of bio-based farnesene (or a compound derived therefrom, or a mixture thereof) and about 3 wt. % of surfactant can be mixed with other components in making a hand cleaner.

In certain embodiments, the present composition comprises water as at least one additional component in the mixture with bio-based farnesene or a compound derived therefrom or a mixture thereof. In certain embodiment, water can be included in the composition as a carrier or diluent. In certain embodiments, water can be included in the composition as a major weight percent component. For example, the present composition can comprise water as a major component (e.g., 83.65 wt. % as a diluent), and bio-based farnesene or a compound derived therefrom or a mixture thereof as a minor component (e.g., 6.0 wt. %). In certain embodiments, the present composition can comprise at least about 50, 55, 60, 65, 70, 75, 80, 85, 90, 95, 96, 97, 98, or 99 wt. % of water and bio-based farnesene or a compound derived therefrom or a mixture thereof as a minor component. In other embodiments, the present composition comprises water as a minor component. For example, the present composition can comprise less than about 50, 45, 40, 35, 30, 25, 20, 15, 10, 5, 4, 3, 2, or 1 wt. % of water and any suitable amount of bio-based farnesene or a compound derived therefrom or a mixture thereof. In certain embodiments, the present composition comprises water in any suitable range selected anywhere between about 0.1 wt. % to about 99.9 wt. %, typically between about 0.5 wt. % to about 99 wt. %, based on the total weight of the composition. The amount of water added to the composition/product depends on end use or application of the composition. For example, for all purpose cleaner and engine degreaser, water may be added as a major component (e.g., at least 80 wt. % or at least 90 wt. %) and bio-based farnesene or a compound derived therefrom or a mixture thereof may be added as a minor weight percent component (e.g., less than 10 wt. % or about 1 wt. % or less). In another example, for all-purpose cleaner concentrate, both water and bio-based farnesene (or a compound derived therefrom, or a mixture thereof) may be added as minor weight percent components (e.g., less than 10 wt. % for both).

In certain embodiments, a composition/product comprises bio-based farnesene (or a compound derived therefrom, or a mixture thereof) and an emulsifier as an additional component. In certain embodiments, an emulsifier can be included in the composition/product as a major weight percent component of the composition/product. For example, a composition/product can comprise at least about 50, 55, 60, 65, 70, 75, 80, 85, 90, 95, 96, 97, 98, or 99 wt. % of emulsifier and a bio-based farnesene (or a compound derived therefrom, or a mixture thereof) as a minor component. In certain embodiments, one or more emulsifiers are included in the composition/product as a minor component. For example, a composition/product can comprise less than about 50, 45, 40, 35, 30, 25, 20, 15, 10, 5, 4, 3, 2, or 1 wt. % of emulsifier and any suitable amount of bio-based farnesene (or a compound derived therefrom, or a mixture thereof). In certain embodiments, a composition/product comprises one or more emulsifiers in any suitable range selected anywhere between about 0.1 wt. % to less than about 50 wt. %, typically between about 1 wt. % to less than about 50 wt. %, based on the total weight of the composition. The amount of emulsifier(s) added to the composition/product depends on end use or application of the composition/product. For example, about 69 wt. % of bio-based farnesene (or a compound derived therefrom, or a mixture thereof) and about 11 wt. % of emulsifier can be mixed with other components in making a solvent degreaser and ink remover as shown in the examples section.

In certain embodiments, a composition/product comprises bio-based farnesene (or a compound derived therefrom, or a mixture thereof) and an emollient as an additional component. In certain embodiments, an emollient can be included in the product as a major weight percent component of the composition/product. For example, a composition/product can comprise at least about 50, 55, 60, 65, 70, 75, 80, 85, 90, 95, 96, 97, 98, or 99 wt. % of emollient and bio-based farnesene (or a compound derived therefrom, or a mixture thereof) as a minor component. In certain embodiments, one or more emollients are included in the composition/product as a minor component. For example, a composition/product can comprise less than about 50, 45, 40, 35, 30, 25, 20, 15, 10, 5, 4, 3, 2, or 1 wt. % of emollient and any suitable amount of bio-based farnesene (or a compound derived therefrom, or a mixture thereof). In certain embodiments, a composition/product comprises one or more emollients in any suitable range selected anywhere between about 0.1 wt. % to less than about 50 wt. %, typically between about 1 wt. % to less than about 50 wt. %, based on the total weight of the composition. The amount of emollient(s) added to the composition/product depends on end use or application of the composition/product.

In certain embodiments, a composition/product comprises bio-based farnesene (or a compound derived therefrom, or a mixture thereof) and a thickener as an additional component. In certain embodiments, a thickener can be included in the product as a major weight percent component of the composition/product. For example, a composition/product can comprise at least about 50, 55, 60, 65, 70, 75, 80, 85, 90, 95, 96, 97, 98, or 99 wt. % of thickener and bio-based farnesene (or a compound derived therefrom, or a mixture thereof) as a minor component. In certain embodiments, one or more thickeners are included in the composition/product as a minor component. For example, a composition/product can comprise less than about 50, 45, 40, 35, 30, 25, 20, 15, 10, 5, 4, 3, 2, or 1 wt. % of thickener and any suitable amount of bio-based farnesene (or a compound derived therefrom, or a mixture thereof). In certain embodiments, a composition/product comprises one or more thickeners in any suitable range selected anywhere between about 0.1 wt. % to less than about 50 wt. %, typically between about 1 wt. % to less than about 50 wt. %, based on the total weight of the composition. The amount of thickener(s) added to the composition/product depends on end use or application of the composition/product. For example, about 90 wt. % of bio-based farnesene (or a compound derived therefrom, or a mixture thereof) about 10 wt. % thickener can be mixed together to make a metal cleaner.

The proportions of components described above are exemplary, and one or more components and/or additives described herein can be mixed together at suitable proportions to provide desired properties to the composition/product.

The compositions/products of the present invention can be manufactured through typical processes such as mixing or blending the composition. Some or all of the ingredients can be mixed together at once, or in some embodiments, the compositions can be prepared through the sequential addition of ingredients to the mixing vessel with low or moderate shearing mixing with order of addition and temperature suitable for the selected ingredients.

In certain embodiments, the end product is in the form of a wipe which is impregnated with the present compositions. The wipe may be in any suitable form, such as nonwoven material, cloth, sponge, or any absorbent material which can be pre-moistened with the present compositions. In some embodiments, the end product may be stored in a container with an applicator, such as a spray nozzle.

The compositions can be used in any method deemed suitable by the practitioner of skill. In certain embodiments, provided herein are methods of cleaning. The methods comprise the step of contacting a substrate with a sufficient amount of a composition and/or a product provided herein to clean the substrate. In certain embodiments, provided herein are methods of degreasing. The methods comprise the step of contacting a substrate with a sufficient amount of a composition and/or a product provided herein to degrease the substrate. Useful substrates include, but are not limited to, domestic and commercial surfaces, skin, hands, floors, walls, engines, clothing, ovens, automobiles, automobile interiors, metals, metal parts, and any other substrate deemed suitable by the practitioner of skill.

In certain embodiments, provided are methods of treating or conditioning skin, hair, or nails. The methods comprise the step of applying to the skin, hair, nails, or any other suitable substrates a sufficient amount of a composition and/or a product provided herein to enhance appearance and/or other properties of the skin, hair, nails, or any other suitable substrates.

In certain embodiments, a kit is provided herein with the present compositions. The kit may comprise the present compositions described herein and instructions for using the composition and/or product. For example, the kit embodiment may include instructions for using the composition neat or instructions for diluting the composition with water (or other suitable diluent) and the appropriate dilution ratio. The kit may further comprise a wipe that is dry or pre-moistened with the present compositions, gloves, or other accessory items.

The materials described herein are also expected to provide a significant benefit to the applications for pesticides and insecticides, hot melt adhesives, sealants, co-monomer in resins and elastomer formulations, synthetic base fluids for drilling mud applications, enhanced oil recovery, an additive in paints and coatings, wood treatment, a processing oil for plasticizing applications, a reactive diluent, a co-monomer in friedel crafts and radical polymerizations, lubricant and lubricant additive, a metathesis cross partner/ substrate, a viscosity modifier, photo and temperature curable initiator system, a solvent and co-solvent for fragrance formulations, antibacterial and/or antifungal additive, and plasticizer in nail polish enamel.

7. EXAMPLES

The following examples provide exemplary formulations for various personal care products and industrial products according to embodiments of the present invention. It is noted that the INCI (International Nomenclature for Cosmetic Ingredients) names for certain materials, such as Neossance® HDD, unsaturated thermal dimer, and Molecule C are proposed names. The INCI name for Neossance® TMD is currently C13-15 alkane, and the INCI name for Myralene™ 10 is currently hydrogenated farnesene instead of INCI names provided in the formulation tables shown below. It is also noted that the term "farnesene" used in the formulation tables below refers to bio-based farnesene, which is biologically produced from microorganisms by fermentation of renewable carbon sources such as sugar. Other $C_{15}$ or $C_{30}$ hydrocarbon compounds or farnesene dimethyl maleate adduct listed in the formulation tables below are derived from the bio-based farnesene. Also, it is noted that materials "as received" can include impurities, residual solvents, humidity (water), or a combination thereof. Thus, the weight percent (wt. %) presented below in the exemplary compositions are based upon the weight percent of the component added to the composition divided by the sum of the weight of all of the components added to form the composition even if the "as received" components may include impurities, residual solvents, humidity (water), or a combination thereof. For example, if component A "as received" and as added to a composition, included 0.5 wt. % residual water, this water would not be counted in calculating the wt. % water in the composition, but only water intentionally added to the composition would be counted in determining the wt. % of water in the composition.

7.1 Example 1: Night Cream Formulations

The following formulations are exemplary night cream formulations for applying to the skin.

| Item No. | Trade Name/Supplier | INCI Name | % by weight |
|---|---|---|---|
| Phase A | | | |
| 1 | Abil WE-09 (Evonik) | Polyglyceryl-4 Isostearate, Cetyl PEG/PPG-10/1 Dimethicone, Hexyl Laurate | 5.00% |
| 2 | Neossance ® HDD (Amyris) | Hydrogenated Dimer Difarnesane (i.e., farnesane dimer) | 15.00% |
| 3 | Abil Wax 9801 (Evonik) | Cetyl Dimethcione | 2.00% |
| Phase B | | | |
| 4 | Deionized water | Water (Aqua) | 73.00% |
| 5 | Sodium Chloride (Univar) | Sodium Chloride | 1.00% |
| 6 | 1,3 Butylene Glycol (Univar) | Butylene Glycol | 3.00% |
| 7 | Mikrokill COS (Arch) | Phenoxyethanol, Chlorphenesin, Caprylyl Glycol | 1.00% |
| | | Total | 100.00% |

| Item No. | Trade Name/Supplier | INCI Name | % by weight |
|---|---|---|---|
| Phase A | | | |
| 1 | Abil WE-09 (Evonik) | Polyglyceryl-4 Isostearate, Cetyl PEG/PPG-10/1 Dimethicone, Hexyl Laurate | 5.00% |
| 2 | unsaturated thermal dimer (Amyris) | farnesene dimer | 15.00% |
| 3 | Abil Wax 9801 (Evonik) | Cetyl Dimethcione | 2.00% |
| Phase B | | | |
| 4 | Deionized water | Water (Aqua) | 73.00% |
| 5 | Sodium Chloride (Univar) | Sodium Chloride | 1.00% |
| 6 | 1,3 Butylene Glycol (Univar) | Butylene Glycol | 3.00% |
| 7 | Mikrokill COS (Arch) | Phenoxyethanol, Chlorphenesin, Caprylyl Glycol | 1.00% |
| | | Total | 100.00% |

| Item No. | Trade Name/Supplier | INCI Name | % by weight |
|---|---|---|---|
| Phase A | | | |
| 1 | Abil WE-09 (Evonik) | Polyglyceryl-4 Isostearate, Cetyl PEG/PPG-10/1 Dimethicone, Hexyl Laurate | 5.00% |
| 2 | Molecule C (Amyris) | farnesene dimethyl maleate adduct | 15.00% |
| 3 | Abil Wax 9801 (Evonik) | Cetyl Dimethcione | 2.00% |
| Phase B | | | |
| 4 | Deionized water | Water (Aqua) | 73.00% |
| 5 | Sodium Chloride (Univar) | Sodium Chloride | 1.00% |
| 6 | 1,3 Butylene Glycol (Univar) | Butylene Glycol | 3.00% |
| 7 | Mikrokill COS (Arch) | Phenoxyethanol, Chlorphenesin, Caprylyl Glycol | 1.00% |
| | | Total | 100.00% |

The night cream formulations are manufactured as follows:
1. Phase A: Into the main beaker, combine items #1 to #3. Start high speed mixing.
2. Phase B: In an auxiliary beaker, combine items #4 to #7 and mix until uniform.
3. Slowly add phase B to phase A. Continue to mix until uniform.

7.2 Example 2: Eye Balm Formulations

The following are exemplary eye balm formulations that can be applied on the skin around the eye.

| Item No. | Trade Name/Supplier | INCI Name | % by weight |
|---|---|---|---|
| Phase A | | | |
| 1 | Deionized water | Water (Aqua) | 52.45% |
| 2 | Dissolvine Na-2-P (Akzo Nobel) | Disodium EDTA | 0.10% |
| 3 | Glycerine, 99.7% USP (Univar) | Glycerin | 10.00% |

-continued

| Item No. | Trade Name/Supplier | INCI Name | % by weight |
|---|---|---|---|
| Phase B | | | |
| 4 | Lipex Shea (AAK) | *Butyrospermum Parkii* (Shea) Butter | 15.00% |
| 5 | Lipo GMS 450 (Lipo) | Glyceryl Stearate | 6.00% |
| 6 | Emulgade PL 68/50 (BASF) | Cetearyl Glucoside, Cetearyl Alcohol | 4.00% |
| 7 | Neossance ® HDD (*Amyris*) | Hydrogenated Dimer Difarnesane (I.e., farnesane dimer) | 6.00% |
| 8 | Jojoba Oil, Colorless (Desert Whale) | *Simmondsia Chinensis* (Jojoba) Seed Oil | 2.00% |
| 9 | Eutanol G (BASF) | Octyldodecanol | 1.00% |
| 10 | Lanette E (BASF) | Sodium Cetearyl Sulfate | 1.00% |
| 11 | Dimethisil DM-350 (Chemsil) | Dimethicone | 1.00% |
| 12 | DL-Alpha Tocopheryl Acetate (DSM) | Tocopheryl Acetate | 0.15% |
| Phase C | | | |
| 13 | Botanistat PF-64 (Botanigenics) | Phenoxyethanol, Ethylhexylglycerin, Caprylyl Glycol, Hexylene Glycol | 1.00% |
| Phase D | | | |
| 14 | Cosmedia SP (BASF) | Sodium Polyacrylate | 0.30% |
| | | Total | 100.00% |

| Item No. | Trade Name/Supplier | INCI Name | % by weight |
|---|---|---|---|
| Phase A | | | |
| 1 | Deionized water | Water (Aqua) | 52.45% |
| 2 | Dissolvine Na-2-P (Akzo Nobel) | Disodium EDTA | 0.10% |
| 3 | Glycerine, 99.7% USP (Univar) | Glycerin | 10.00% |
| Phase B | | | |
| 4 | Lipex Shea (AAK) | *Butyrospermum Parkii* (Shea) Butter | 15.00% |
| 5 | Lipo GMS 450 (Lipo) | Glyceryl Stearate | 6.00% |
| 6 | Emulgade PL 68/50 (BASF) | Cetearyl Glucoside, Cetearyl Alcohol | 4.00% |
| 7 | unsaturated thermal dimer (*Amyris*) | farnesene dimer | 6.00% |
| 8 | Jojoba Oil, Colorless (Desert Whale) | *Simmondsia Chinensis* (Jojoba) Seed Oil | 2.00% |
| 9 | Eutanol G (BASF) | Octyldodecanol | 1.00% |
| 10 | Lanette E (BASF) | Sodium Cetearyl Sulfate | 1.00% |
| 11 | Dimethisil DM-350 (Chemsil) | Dimethicone | 1.00% |
| 12 | DL-Alpha Tocopheryl Acetate (DSM) | Tocopheryl Acetate | 0.15% |
| Phase C | | | |
| 13 | Botanistat PF-64 (Botanigenics) | Phenoxyethanol, Ethylhexylglycerin, Caprylyl Glycol, Hexylene Glycol | 1.00% |
| Phase D | | | |
| 14 | Cosmedia SP (BASF) | Sodium Polyacrylate | 0.30% |
| | | Total | 100.00% |

| Item No. | Trade Name/Supplier | INCI Name | % by weight |
|---|---|---|---|
| Phase A | | | |
| 1 | Deionized water | Water (Aqua) | 52.45% |
| 2 | Dissolvine Na-2-P (Akzo Nobel) | Disodium EDTA | 0.10% |
| 3 | Glycerine, 99.7% USP (Univar) | Glycerin | 10.00% |
| Phase B | | | |
| 4 | Lipex Shea (AAK) | *Butyrospermum Parkii* (Shea) Butter | 15.00% |
| 5 | Lipo GMS 450 (Lipo) | Glyceryl Stearate | 6.00% |
| 6 | Emulgade PL 68/50 (BASF) | Cetearyl Glucoside, Cetearyl Alcohol | 4.00% |
| 7 | Molecule C (*Amyris*) | farnesene dimethyl maleate adduct | 6.00% |
| 8 | Jojoba Oil, Colorless (Desert Whale) | *Simmondsia Chinensis* (Jojoba) Seed Oil | 2.00% |
| 9 | Eutanol G (BASF) | Octyldodecanol | 1.00% |
| 10 | Lanette E (BASF) | Sodium Cetearyl Sulfate | 1.00% |
| 11 | Dimethisil DM-350 (Chemsil) | Dimethicone | 1.00% |
| 12 | DL-Alpha Tocopheryl Acetate (DSM) | Tocopheryl Acetate | 0.15% |
| Phase C | | | |
| 13 | Botanistat PF-64 (Botanigenics) | Phenoxyethanol, Ethylhexylglycerin, Caprylyl Glycol, Hexylene Glycol | 1.00% |
| Phase D | | | |
| 14 | Cosmedia SP (BASF) | Sodium Polyacrylate | 0.30% |
| | | Total | 100.00% |

The eye balm formulations are manufactured as follows:

1. Phase A: Combine items #1 to #3 and mix until uniform. Heat to 75° C.

2. Phase B: In an auxiliary beaker, combine items #4 to #12 and heat to 75° C. Mix until uniform.

3. When both phases are at 75° C., add phase B to phase A. Mix until uniform. Cool to 40° C.

4. Phase C: At 40° C., add item #13.

5. Phase D: Sprinkle in item #14 and mix until uniform.

6. QS batch with DI water and cool to 35° C.

7.3 Example 3: Lip Gloss Formulations

The following are exemplary lip gloss formulations that can be applied to the lip.

| Item No. | Trade Name/Supplier | INCI Name | % by weight |
|---|---|---|---|
| Phase A | | | |
| 1 | Neossance ® HDD (*Amyris*) | Hydrogenated Dimer Difarnesane (i.e., farnesene dimer) | 18.00% |
| 2 | Versagel ME-750 (Calumet/Penreco) | Hydrogenated Polyisobutene, Butylene/Ethylene/Styrene Copolymer, Ethylene/Propylene/Styrene Copolymer | 24.90% |
| 3 | Softisan 649 (Sasol) | Bis-Diglyceryl Polyacyladipate-2 | 16.00% |
| 4 | Crodamol PTIS (Croda) | Pentaerythrityl Tetraisostearate | 12.00% |
| 5 | Indopol H-100 (Lipo) | Polybutene | 15.00% |

-continued

| Item No. | Trade Name/Supplier | INCI Name | % by weight |
|---|---|---|---|
| 6 | Super Sterol Ester (Croda) | C10-30 Cholesterol/Lanosterol Esters | 5.00% |
| 7 | Orisil 200 (Orisil) | Amorphous Fumed Silica | 1.00% |
| | | Phase B | |
| 8 | Ozokerite Wax SP-1020P (Strahl and Pitsch) | Ozokerite | 3.00% |
| 9 | Candelilla Wax SP-75 (Strahl and Pitsch) | *Euphorbia Cerifera* (Candelilla) Wax | 3.00% |
| 10 | Lexgard O (Inolex) | Caprylyl Glycol | 0.50% |
| 11 | Bronidox 1160 (BASF) | Phenoxyethanol | 0.50% |
| 12 | DL-Alpha Tocopheryl Acetate (DSM) | Tocopheryl Acetate | 0.10% |
| 13 | Pomegranate Blackberry FL OS 103-31160 (Bell Flavors and Fragrances) | Flavor | 0.50% |
| | | Phase C | |
| 14 | FAS55ERSI (KOBO) | Iron Oxides (CI77491), Cyclopentasiloxane, PEG/PPG 18/18 Dimethicone | 0.50% |
| | | Total | 100.00% |

| Item No. | Trade Name/Supplier | INCI Name | % by weight |
|---|---|---|---|
| | | Phase A | |
| 1 | unsaturated thermal dimer (*Amyris*) | farnesene dimer | 18.00% |
| 2 | Versagel ME-750 (Calumet/Penreco) | Hydrogenated Polyisobutene, Butylene/Ethylene/Styrene Copolymer, Ethylene/Propylene/Styrene Copolymer | 24.90% |
| 3 | Softisan 649 (Sasol) | Bis-Diglyceryl Polyacyladipate-2 | 16.00% |
| 4 | Crodamol PTIS (Croda) | Pentaerythrityl Tetraisostearate | 12.00% |
| 5 | Indopol H-100 (Lipo) | Polybutene | 15.00% |
| 6 | Super Sterol Ester (Croda) | C10-30 Cholesterol/Lanosterol Esters | 5.00% |
| 7 | Orisil 200 (Orisil) | Amorphous Fumed Silica | 1.00% |
| | | Phase B | |
| 8 | Ozokerite Wax SP-1020P (Strahl and Pitsch) | Ozokerite | 3.00% |
| 9 | Candelilla Wax SP-75 (Strahl and Pitsch) | *Euphorbia Cerifera* (Candelilla) Wax | 3.00% |
| 10 | Lexgard O (Inolex) | Caprylyl Glycol | 0.50% |
| 11 | Bronidox 1160 (BASF) | Phenoxyethanol | 0.50% |
| 12 | DL-Alpha Tocopheryl Acetate (DSM) | Tocopheryl Acetate | 0.10% |
| 13 | Pomegranate Blackberry FL OS 103-31160 (Bell Flavors and Fragrances) | Flavor | 0.50% |
| | | Phase C | |
| 14 | FAS55ERSI (KOBO) | Iron Oxides (CI77491), Cyclopentasiloxane, PEG/PPG 18/18 Dimethicone | 0.50% |
| | | Total | 100.00% |

| Item No. | Trade Name/Supplier | INCI Name | % by weight |
|---|---|---|---|
| | | Phase A | |
| 1 | Molecule C (*Amyris*) | farnesene dimethyl maleate adduct | 18.00% |
| 2 | Versagel ME-750 (Calumet/Penreco) | Hydrogenated Polyisobutene, Butylene/Ethylene/Styrene Copolymer, Ethylene/Propylene/Styrene Copolymer | 24.90% |
| 3 | Softisan 649 (Sasol) | Bis-Diglyceryl Polyacyladipate-2 | 16.00% |
| 4 | Crodamol PTIS (Croda) | Pentaerythrityl Tetraisostearate | 12.00% |
| 5 | Indopol H-100 (Lipo) | Polybutene | 15.00% |
| 6 | Super Sterol Ester (Croda) | C10-30 Cholesterol/Lanosterol Esters | 5.00% |
| 7 | Orisil 200 (Orisil) | Amorphous Fumed Silica | 1.00% |
| | | Phase B | |
| 8 | Ozokerite Wax SP-1020P (Strahl and Pitsch) | Ozokerite | 3.00% |
| 9 | Candelilla Wax SP-75 (Strahl and Pitsch) | *Euphorbia Cerifera* (Candelilla) Wax | 3.00% |
| 10 | Lexgard O (Inolex) | Caprylyl Glycol | 0.50% |
| 11 | Bronidox 1160 (BASF) | Phenoxyethanol | 0.50% |
| 12 | DL-Alpha Tocopheryl Acetate (DSM) | Tocopheryl Acetate | 0.10% |
| 13 | Pomegranate Blackberry FL OS 103-31160 (Bell Flavors and Fragrances) | Flavor | 0.50% |
| | | Phase C | |
| 14 | FAS55ERSI (KOBO) | Iron Oxides (CI77491), Cyclopentasiloxane, PEG/PPG 18/18 Dimethicone | 0.50% |
| | | Total | 100.00% |

The lip gloss formulations are manufactured as follows:

1. Phase A: Combine items #1 to #7 and mix until uniform. Heat to 75° C.-80° C.
2. Phase B: At 75° C.-80° C., add items #8 to #13.
3. Phase C: Add item #14 and mix until uniform.
4. Maintain temperature at 75° C.-80° C. and fill immediately.

7.4 Example 4: Anti-Frizz Treatment Formulations

The following are exemplary anti-frizz treatment formulations for treating hair.

| Item No. | Trade Name/Supplier | INCI Name | % by weight |
|---|---|---|---|
| 1 | Neossance ® TMD (*Amyris*) | Trimethyldodecane (i.e., farnesane) | 40.00% |
| 2 | Dow Corning 1403 (Dow Corning) | Dimethicone, Dimethiconol | 50.00% |
| 3 | Dow Corning 556 (Dow Corning) | Phenyl Trimethicone | 5.00% |
| 4 | Crodamol STS (Croda) | PPG-3 Benzyl Ether Myristate | 5.00% |
| | | Total | 100.00% |

| Item No. | Trade Name/Supplier | INCI Name | % by weight |
|---|---|---|---|
| 1 | Myralene ™ 10 (*Amyris*) | partially hydrogenated farnesene (e.g., dihydrofarnesene) | 40.00% |
| 2 | Dow Corning 1403 (Dow Corning) | Dimethicone, Dimethiconol | 50.00% |
| 3 | Dow Corning 556 (Dow Corning) | Phenyl Trimethicone | 5.00% |
| 4 | Crodamol STS (Croda) | PPG-3 Benzyl Ether Myristate | 5.00% |
|  |  | Total | 100.00% |

The anti-frizz hair formulations are manufactured by combining items #1 to #4 and mixing them until uniform.

7.5 Example 5: Body Lotion Formulations

The following are exemplary body lotion formulations that can be applied on the skin.

| Item No. | Trade Name/Supplier | INCI Name | % by weight |
|---|---|---|---|
| Phase A |||||
| 1 | Abil WE-09 (Evonik) | Polyglyceryl-4 Isostearate, Cetyl PEG/PPG-10/1 Dimethicone, Hexyl Laurate | 5.00% |
| 2 | Myritol 312 (BASF) | Caprylic/Capric Triglyceride | 7.00% |
| 3 | Neossance ® TMD (*Amyris*) | Trimethyldodecane (i.e., farnesane) | 9.00% |
| 4 | Abil Wax 9801 (Evonik) | Cetyl Dimethcione | 2.00% |
| Phase B |||||
| 5 | Deionized water | Water (Aqua) | 72.00% |
| 6 | Sodium Chloride (Univar) | Sodium Chloride | 1.00% |
| 7 | 1,3 Butylene Glycol (Univar) | Butylene Glycol | 3.00% |
| 8 | Mikrokill COS (Arch) | Phenoxyethanol, Chlorphenesin, Caprylyl Glycol | 1.00% |
|  |  | Total | 100.00% |

| Item No. | Trade Name/Supplier | INCI Name | % by weight |
|---|---|---|---|
| Phase A |||||
| 1 | Abil WE-09 (Evonik) | Polyglyceryl-4 Isostearate, Cetyl PEG/PPG-10/1 Dimethicone, Hexyl Laurate | 5.00% |
| 2 | Myritol 312 (BASF) | Caprylic/Capric Triglyceride | 7.00% |
| 3 | Myralene ™ 10 (*Amyris*) | partially hydrogenated farnesene (e.g., dihydrofarnesene) | 9.00% |
| 4 | Abil Wax 9801 (Evonik) | Cetyl Dimethcione | 2.00% |
| Phase B |||||
| 5 | Deionized water | Water (Aqua) | 72.00% |
| 6 | Sodium Chloride (Univar) | Sodium Chloride | 1.00% |
| 7 | 1,3 Butylene Glycol (Univar) | Butylene Glycol | 3.00% |
| 8 | Mikrokill COS (Arch) | Phenoxyethanol, Chlorphenesin, Caprylyl Glycol | 1.00% |
|  |  | Total | 100.00% |

The anti-frizz hair formulations are manufactured as follows:

1. Phase A: Into the main beaker, combine items #1 to #4. Start high speed mixing.

2. Phase B: In an auxiliary beaker, combine items #5 to #8 and mix until uniform.

3. Slowly add phase B to phase A. Continue to mix until uniform.

7.6 Example 6: Face Serum Formulations

The following are exemplary face serum formulations that can be applied to the skin, particularly on the face.

| Item No. | Trade Name/Supplier | INCI Name | % by weight |
|---|---|---|---|
| Phase A |||||
| 1 | Deionized water | Water (Aqua) | 78.50% |
| 2 | Dissolvine Na-2-P (Akzo Nobel) | Disodium EDTA | 0.10% |
| 3 | Hydrolite-5 (Symrise) | Pentylene Glycol | 3.00% |
| 4 | Sepinov EMT-10 (Seppic) | Hydroxyethyl Acrylate/ Sodium Acryloyldimethyl Taurate Copolymer, Sodium Isostearate, Water, Polysorbate 60 | 1.00% |
| Phase B |||||
| 5 | Keltrol CG (CP Kelco) | Xanthan Gum | 0.20% |
| 6 | Glycerine, 99.7% (Univar) | Glycerin | 3.00% |
| 7 | 1,3 Butylene Glycol (Univar) | Butylene Glycol | 3.00% |
| Phase C |||||
| 8 | Neossance ® TMD (*Amyris*) | Trimethyldodecane (i.e., farnesane) | 5.00% |
| 9 | Dracorin GOC 683541 (Symrise) | Caprylic/Capric Triglyceride, Glyceryl Oleate Citrate | 1.50% |
| Phase D |||||
| 10 | Covabead Glass (Sensient) | Magnesium Silicate | 1.50% |
| Phase E |||||
| 11 | Botanistat PF-64 (Botanigenics) | Phenoxyethanol, Hexylene Glycol, Ethylhexylglycerin, Caprylyl Glycol | 1.00% |
| 12 | Fucogel 1.5P (Solabia) | Biosaccharide Gum-1 | 1.00% |
| Phase F |||||
| 13 | Deionized water | Water (Aqua) | 1.00% |
| 14 | Potassium Sorbate FCC (Univar) | Potassium Sorbate | 0.20% |
|  |  | Total | 100.00% |

| Item No. | Trade Name/Supplier | INCI Name | % by weight |
|---|---|---|---|
| | | Phase A | |
| 1 | Deionized water | Water (Aqua) | 78.50% |
| 2 | Dissolvine Na-2-P (Akzo Nobel) | Disodium EDTA | 0.10% |
| 3 | Hydrolite-5 (Symrise) | Pentylene Glycol | 3.00% |
| 4 | Sepinov EMT-10 (Seppic) | Hydroxyethyl Acrylate/ Sodium Acryloyldimethyl Taurate Copolymer, Sodium Isostearate, Water, Polysorbate 60 | 1.00% |
| | | Phase B | |
| 5 | Keltrol CG (CP Kelco) | Xanthan Gum | 0.20% |
| 6 | Glycerine, 99.7% (Univar) | Glycerin | 3.00% |
| 7 | 1,3 Butylene Glycol (Univar) | Butylene Glycol | 3.00% |
| | | Phase C | |
| 8 | Myralene ™ 10 (*Amyris*) | Partially hydrogenated farnesene (e.g., dihydrofarnesene) | 5.00% |
| 9 | Dracorin GOC 683541 (Symrise) | Caprylic/Capric Triglyceride, Glyceryl Oleate Citrate | 1.50% |
| | | Phase D | |
| 10 | Covabead Glass (Sensient) | Magnesium Silicate | 1.50% |
| | | Phase E | |
| 11 | Botanistat PF-64 (Botanigenics) | Phenoxyethanol, Hexylene Glycol, Ethylhexylglycerin, Caprylyl Glycol | 1.00% |
| 12 | Fucogel 1.5P (Solabia) | Biosaccharide Gum-1 | 1.00% |
| | | Phase F | |
| 13 | Deionized water | Water (Aqua) | 1.00% |
| 14 | Potassium Sorbate FCC (Univar) | Potassium Sorbate | 0.20% |
| | | Total | 100.00% |

The face serum formulations are manufactured as follows:
1. Phase A: Into the main beaker, combine items #1 to #3. Start high speed mixing.
2. Sprinkle in item #4 and mix until uniform. Heat to 75° C.
3. Phase B: Combine items #5 to #7. Mix into a uniform slurry, and add to phase A.
4. Phase C: Combine items #8 and #9, mix until uniform, and then add to batch. Cool to 60° C.
5. Phase D: At 60° C., add item #10. Cool to 40° C. Mix until uniform.
6. Phase E: At 40° C., add items #11 to #12. Mix until uniform.
7. Phase F: Combine items #13 and #14 and add to batch. Mix until uniform.
8. QS batch with DI water and cool to 35° C.

7.7 Example 7: Industrial or Consumer Product Formulations Comprising Bio-Based Farnesene The following are various industrial and consumer product formulations comprising bio-based farnesene as a solvent. Non-limiting examples of industrial and consumer product formulations that comprise bio-based farnesene as a solvent include hard surface heavy duty cleaner, pumice hand cleaner, smooth hand cleaner, graffiti remover, solvent degreaser, bug and tar remover, oven cleaner, interior auto cleaner, all-purpose cleaner, metal cleaning fluid, scrubbing wipe, and the like.

| Hard Surface Heavy Duty Cleaner | | | |
|---|---|---|---|
| Ingredient | % | Ingredient Function | Application |
| Farnesane | 35 | Solvent | For clean-up of heavy grease surfaces in industrial applications |
| Tomadol 25-7 | 3 | Surfactant | |
| Videt ME-80 | 20 | Surfactant | |
| Deionized Water | 42 | Diluent | |

| Pumice Hand Cleaner | | | |
|---|---|---|---|
| Ingredient | % | Ingredient Function | Application |
| Farnesane | 6.14 | Solvent | A waterless hand cleaner containing abrasive for heavy duty cleaning in industrial environments |
| Carbopol Ultrez 10 | 0.3 | Thickener | |
| Deionized Water | 82.81 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Pumice | 4.5 | Abrasive | |
| Microcare MTO | 0.15 | Preservative | |
| *Amyris* Squalane | 1 | Emollient | |
| Givaduan Fragrance | 0.1 | Fragrance | |
| d-Limonene | 0.95 | Fragrance | |

| Smooth Hand Cleaner | | | |
|---|---|---|---|
| Ingredient | % | Ingredient Function | Application |
| Farnesane | 6.14 | Solvent | A waterless hand cleaner for heavy duty cleaning in industrial environments |
| Carbopol Ultrez 10 | 0.3 | Thickener | |
| Deionized Water | 87.31 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Microcare MTO | 0.15 | Preservative | |
| *Amyris* Squalane | 1 | Emollient | |
| Givaduan Fragrance | 0.1 | Fragrance | |
| d-Limonene | 0.95 | Fragrance | |

| Graffiti Remover | | | |
|---|---|---|---|
| Ingredient | % | Ingredient Function | Application |
| Farnesane | 18 | Solvent | A cleaner for removing graffiti from painted surfaces |
| Tomadol 25-7 | 0.9 | Surfactant | |
| DBE-LVP | 18 | Solvent | |
| Isopar M | 63.1 | Diluent | |

| Solvent Degreaser #1 | | | |
|---|---|---|---|
| Ingredient | % | Ingredient Function | Application |
| Farnesane | 9.5 | Solvent | A spray cleaner for removing tars, greases and inks surfaces |
| DBE-LVP | 10 | Solvent | |
| Eastman Omnia Solvent | 3 | Surfactant | |
| Sasol LPA-210 | 77.5 | Diluent | |
| d-Limonene (optional) | Optional 1-2% | Fragrance | |

Solvent Degreaser #2

| Ingredient | % | Ingredient Function | Application |
|---|---|---|---|
| Farnesane | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional 1-2% | Fragrance | |

Solvent Degreaser #3

| Ingredient | % | Ingredient Function | Application |
|---|---|---|---|
| Farnesane | 9.5 | Solvent | A biodegradable spray cleaner for removing tars, greases and inks surfaces |
| DBE-LVP | 10 | Solvent | |
| Eastman Omnia Solvent | 3 | Surfactant | |
| KETRUL D 100 | 77.5 | Diluent | |
| d-Limonene (optional) | Optional 1-2% | Fragrance | |

Solvent Degreaser #4

| Ingredient | % | Ingredient Function | Application |
|---|---|---|---|
| Farnesane | 9 | Solvent | A spray cleaner for removing tars, greases and inks surfaces |
| DBE-LVP | 9 | Solvent | |
| Rhodocal IPAM | 0.3 | Surfactant | |
| Isopar M | 81.7 | Diluent | |
| d-Limonene (optional) | Optional 1-2% | Fragrance | |

Solvent Degreaser #5

| Ingredient | % | Ingredient Function | Application |
|---|---|---|---|
| Farnesane | 9 | Solvent | A biodegradable spray cleaner for removing tars, greases and inks surfaces |
| DBE-LVP | 9 | Solvent | |
| Rhodocal IPAM | 0.3 | Surfactant | |
| HYDROSEAL G 232 H | 81.7 | Diluent | |
| d-Limonene (optional) | Optional 1-2% | Fragrance | |

Solvent Degreaser #6

| Ingredient | % | Ingredient Function | Application |
|---|---|---|---|
| Farnesane | 9 | Solvent | A biodegradable spray cleaner for removing tars, greases and inks surfaces |
| DBE-LVP | 9 | Solvent | |
| Rhodocal IPAM | 0.3 | Surfactant | |
| KETRUL D 100 | 81.7 | Diluent | |
| d-Limonene (optional) | Optional 1-2% | Fragrance | |

Bug and Tar Remover

| Ingredient | % | Ingredient Function | Application |
|---|---|---|---|
| Farnesane | 35 | Solvent | Heavy duty external car cleaner for removal of bugs and tar from automotive vehicles |
| Tomadol 25-7 | 3 | Surfactant | |
| Windet ME-80 | 20 | Surfactant | |
| Deionized Water | 42 | Diluent | |

Oven Cleaner

| Ingredient | % | Ingredient Function | Application |
|---|---|---|---|
| Deionized Water | 87.73 | Diluent | Spray cleaner to help remove stains on household ovens |
| Farnesane | 2 | Solvent | |
| Kelzan ASX-T | 0.35 | Thickener | |
| Sodium Bicarbonate | 2 | Alkaline Buffer | |
| Sodium Metasilicate Pentahydrate | 0.2 | Alkaline Buffer | |
| Trilon M liquid | 0.25 | Chelator | |
| Videt Q3 | 5 | Surfactant | |
| Potassium Hydroxide (45%) | 2.47 | Alkaline Builder | |

Interior Auto Cleaner

| Ingredient | % | Ingredient Function | Application |
|---|---|---|---|
| Deionized Water | 95.5 | Diluent | A spray cleaner for car interior cleaning |
| Sodium Citrate | 1.0 | Alkaline Buffer | |
| Farnesene | 0.5 | Solvent | |
| AMPHOSOL ® CA | 3.0 | Surfactant | |

All-Purpose Cleaner #1

| Ingredient | % | Ingredient Function | Application |
|---|---|---|---|
| Deionized Water | 91.9 | Diluent | Formulation for Heavy duty industrial cleaning applications pH ~10.9, Cloud pt = 35 C. |
| Trilon M liquid | 0.5 | Chelator | |
| Potassium Carbonate | 0.6 | Alkaline Builder | |
| Tergitol 15-S-7 | 4.0 | Surfactant | |
| Amphoteric 400 | 2 | Surfactant | |
| Farnesene | 1 | Solvent | |

All-Purpose Cleaner #2

| Ingredient | % | Ingredient Function | Application |
|---|---|---|---|
| Deionized Water | 92.9 | Diluent | Formulation for Heavy duty industrial cleaning applications pH ~10.9, Cloud pt = 40 C. |
| Trilon M liquid | 0.5 | Chelator | |
| Potassium Carbonate | 0.6 | Alkaline Builder | |
| Ecosurf EH-6 | 4.0 | Surfactant | |
| Amphoteric 400 | 1 | Surfactant | |
| Farnesene | 1 | Solvent | |

All-Purpose Cleaner #3

| Ingredient | % | Ingredient Function | Application |
|---|---|---|---|
| Deionized Water | 91.9 | Diluent | Formulation for Heavy duty industrial cleaning applications pH ~10.9, Cloud pt = 34 C. |
| Trilon M liquid | 0.5 | Chelator | |
| Potassium Carbonate | 0.6 | Alkaline Builder | |
| Ecosurf SA-7 | 4.0 | Surfactant | |
| Amphoteric 400 | 2 | Surfactant | |
| Farnesene | 1 | Solvent | |

All-Purpose Cleaner #4

| Ingredient | % | Ingredient Function | Application |
|---|---|---|---|
| Deionized Water | 90.9 | Diluent | Formulation for Heavy duty industrial cleaning applications pH ~10.9, Cloud pt = 45 C. |
| Trilon M liquid | 0.5 | Chelator | |
| Potassium Carbonate | 0.6 | Alkaline Builder | |
| Tergitol 15-S-7 | 4.0 | Surfactant | |
| Alkatrope SXS-40 | 3.0 | Surfactant | |
| Farnesene | 1 | Solvent | |

All-Purpose Cleaner #5

| Ingredient | % | Ingredient Function | Application |
|---|---|---|---|
| Deionized Water | 90.2 | Diluent | Formulation for Heavy duty industrial cleaning applications pH ~13-14 Cloud pt = 51 C. |
| Trilon M liquid | 1.0 | Alkaline Buffer | |
| Sodium Metasilicate Pentahydrate | 2.0 | Alkaline Builder | |
| Potassium Hydroxide (45%) | 2.0 | Solvent | |
| Videt Q3 | 4.1 | Surfactant | |
| Farnesene | 0.75 | Chelator | |

All-Purpose Cleaner Concentrate

| Ingredient | % | Ingredient Function | Application |
|---|---|---|---|
| Farnesene | 35 | Solvent | Dilutable formulation for light duty industrial cleaning applications |
| Videt ME-80 | 20 | Surfactant | |
| Tomadol 25-7 | 3 | Surfactant | |
| Deionized Water | 42 | Diluent | |

Metal Cleaning Fluid

| Ingredient | % | Ingredient Function | Application |
|---|---|---|---|
| Farnesene | 90 | Solvent | Metal parts cleaning (e.g. post machining applications) |
| Linear Alcohol (C12-15) Ethoxylate, POE-7 | 10 | Thickener | |

Scrubbing Wipe #1

| Ingredient | % | Ingredient Function | Application |
|---|---|---|---|
| Deionized Water | 91.875 | Diluent | A wipe for tough soil hand and surface cleaning. |
| Stepan BIO-SOFT N1-7 | 2.20 | Surfactant | |
| Eastman Omnia | 2.00 | Solvent | |
| Farnesene | 1.20 | Solvent | |
| BIO-SOFT EC-639 | 0.88 | Surfactant | |
| AkzoNobel Ethoquad C/25 | 0.73 | Surfactant | |
| Glycerin | 0.50 | Humectant | |
| Stepan Ammonyx LO | 0.18 | Surfactant | |
| Fragrance | 0.15 | Fragrance | |
| Neossance ® Hemisqualane | 0.10 | Emollient | |
| Neossance ® Squalane | 0.10 | Emollient | |
| Acticide MBS | <0.10 | Preservative | |

Scrubbing Wipe #2

| Ingredient | % | Ingredient Function | Application |
|---|---|---|---|
| Pentex 99 (DOSS) | 3.00 | Anionic Emulsifier | A wipe for tough soil hand and surface cleaning. |
| Tergitol 15-S-5 | 2.00 | Non-ionic emulsifier | |
| Farnesene | 2.75 | Solvent | |
| Deionized Water | 92.10 | Diluent | |
| Acticide SPX | 0.15 | Preservative | |

7.8 Example 8: Industrial or Consumer Product Formulations Comprising Farnesene Dimethyl Maleate Adduct The following are various industrial and consumer product formulations comprising farnesene dimethyl maleate adduct as a solvent. Non-limiting examples of industrial and consumer product formulations that comprise farnesene dimethyl maleate adduct (e.g., Myralene™ 210) as a solvent include hard surface heavy duty cleaner, pumice hand cleaner, smooth hand cleaner, graffiti remover, solvent degreaser, bug and tar remover, oven cleaner, interior auto cleaner, all-purpose cleaner, metal cleaning fluid, scrubbing wipe, and the like.

Hard Surface Heavy Duty Cleaner

| Ingredient | % | Ingredient Function | Application |
|---|---|---|---|
| farnesene dimethyl maleate adduct | 35 | Solvent | For clean-up of heavy grease surfaces in industrial applications |
| Tomadol 25-7 | 3 | Surfactant | |
| Videt ME-80 | 20 | Surfactant | |
| Deionized Water | 42 | Diluent | |

Pumice Hand Cleaner

| Ingredient | % | Ingredient Function | Application |
|---|---|---|---|
| farnesene dimethyl maleate adduct | 6.14 | Solvent | A waterless hand cleaner containing abrasive for heavy duty cleaning in industrial environments |
| Carbopol Ultrez 10 | 0.3 | Thickener | |
| Deionized Water | 82.81 | Diluent | |
| Acusol 820 | 1.25 | Surfactant | |

Pumice Hand Cleaner

| Ingredient | % | Ingredient Function | Application |
|---|---|---|---|
| DBE-LVP | 0.3 | Solvent | |
| Tomadol 25-7 | 1.75 | Surfactant | |
| Triethanolamine (to pH 7.0-7.9) | 0.75 | Neutralizer | |
| Pumice | 4.5 | Abrasive | |
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Smooth Hand Cleaner

| Ingredient | % | Ingredient Function | Application |
|---|---|---|---|
| farnesene dimethyl maleate adduct | 6.14 | Solvent | A waterless hand cleaner for heavy duty cleaning in industrial environments |
| Carbopol Ultrez 10 | 0.3 | Thickener | |
| Deionized Water | 87.31 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Graffiti Remover

| Ingredient | % | Ingredient Function | Application |
|---|---|---|---|
| farnesene dimethyl maleate adduct | 18 | Solvent | A cleaner for removing graffiti from painted surfaces |
| Tomadol 25-7 | 0.9 | Surfactant | |
| DBE-LVP | 18 | Solvent | |
| Isopar M | 63.1 | Diluent | |

Solvent Degreaser #1

| Ingredient | % | Ingredient Function | Application |
|---|---|---|---|
| farnesene dimethyl maleate adduct | 9.5 | Solvent | A spray cleaner for removing tars, greases and inks surfaces |
| DBE-LVP | 10 | Solvent | |
| Eastman Omnia Solvent | 3 | Surfactant | |
| Sasol LPA-210 | 77.5 | Diluent | |
| d-Limonene (optional) | Optional 1-2% | Fragrance | |

Solvent Degreaser #2

| Ingredient | % | Ingredient Function | Application |
|---|---|---|---|
| farnesene dimethyl maleate adduct | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional 1-2% | Fragrance | |

Solvent Degreaser #3

| Ingredient | % | Ingredient Function | Application |
|---|---|---|---|
| farnesene dimethyl maleate adduct | 9.5 | Solvent | A biodegradable spray cleaner for removing tars, greases and inks surfaces |
| DBE-LVP | 10 | Solvent | |
| Eastman Omnia Solvent | 3 | Surfactant | |
| KETRUL D 100 | 77.5 | Diluent | |
| d-Limonene (optional) | Optional 1-2% | Fragrance | |

Solvent Degreaser #4

| Ingredient | % | Ingredient Function | Application |
|---|---|---|---|
| farnesene dimethyl maleate adduct | 9 | Solvent | A spray cleaner for removing tars, greases and inks surfaces |
| DBE-LVP | 9 | Solvent | |
| Rhodocal IPAM | 0.3 | Surfactant | |
| Isopar M | 81.7 | Diluent | |
| d-Limonene (optional) | Optional 1-2% | Fragrance | |

Solvent Degreaser #5

| Ingredient | % | Ingredient Function | Application |
|---|---|---|---|
| farnesene dimethyl maleate adduct | 9 | Solvent | A biodegradable spray cleaner for removing tars, greases and inks surfaces |
| DBE-LVP | 9 | Solvent | |
| Rhodocal IPAM | 0.3 | Surfactant | |
| HYDROSEAL G 232 H | 81.7 | Diluent | |
| d-Limonene (optional) | Optional 1-2% | Fragrance | |

Solvent Degreaser #6

| Ingredient | % | Ingredient Function | Application |
|---|---|---|---|
| farnesene dimethyl maleate adduct | 9 | Solvent | A biodegradable spray cleaner for removing tars, greases and inks surfaces |
| DBE-LVP | 9 | Solvent | |
| Rhodocal IPAM | 0.3 | Surfactant | |
| KETRUL D 100 | 81.7 | Diluent | |
| d-Limonene (optional) | Optional 1-2% | Fragrance | |

Bug and Tar Remover

| Ingredient | % | Ingredient Function | Application |
|---|---|---|---|
| farnesene dimethyl maleate adduct | 35 | Solvent | Heavy duty external car cleaner for removal of bugs and tar from automotive vehicles |
| Tomadol 25-7 | 3 | Surfactant | |
| Windet ME-80 | 20 | Surfactant | |
| Deionized Water | 42 | Diluent | |

Oven Cleaner

| Ingredient | % | Ingredient Function | Application |
|---|---|---|---|
| Deionized Water | 87.73 | Diluent | Spray cleaner to help remove stains on household ovens |
| farnesene dimethyl maleate adduct | 2 | Solvent | |
| Kelzan ASX-T | 0.35 | Thickener | |
| Sodium Biocarbonate | 2 | Alkaline Buffer | |
| Sodium Metasilicate Pentahydrate | 0.2 | Alkaline Buffer | |
| Trilon M liquid | 0.25 | Chelator | |
| Videt Q3 | 5 | Surfactant | |
| Potassium Hydroxide (45%) | 2.47 | Alkaline Builder | |

Interior Auto Cleaner

| Ingredient | % | Ingredient Function | Application |
|---|---|---|---|
| Deionized Water | 95.5 | Diluent | A spray cleaner for car interior cleaning |
| Sodium Citrate | 1.0 | Alkaline Buffer | |
| farnesene dimethyl maleate adduct | 0.5 | Solvent | |
| AMPHOSOL ® CA | 3.0 | Surfactant | |

All-Purpose Cleaner #1

| Ingredient | % | Ingredient Function | Application |
|---|---|---|---|
| Deionized Water | 91.9 | Diluent | Formulation for Heavy duty industrial cleaning applications pH ~10.9, Cloud pt = 35 C. |
| Trilon M liquid | 0.5 | Chelator | |
| Potassium Carbonate | 0.6 | Alkaline Builder | |
| Tergitol 15-S-7 | 4.0 | Surfactant | |
| Amphoteric 400 | 2 | Surfactant | |
| farnesene dimethyl maleate adduct | 1 | Solvent | |

All-Purpose Cleaner #2

| Ingredient | % | Ingredient Function | Application |
|---|---|---|---|
| Deionized Water | 92.9 | Diluent | Formulation for Heavy duty industrial cleaning applications pH ~10.9, Cloud pt = 40 C. |
| Trilon M liquid | 0.5 | Chelator | |
| Potassium Carbonate | 0.6 | Alkaline Builder | |
| Ecosurf EH-6 | 4.0 | Surfactant | |
| Amphoteric 400 | 1 | Surfactant | |
| farnesene dimethyl maleate adduct | 1 | Solvent | |

All-Purpose Cleaner #3

| Ingredient | % | Ingredient Function | Application |
|---|---|---|---|
| Deionized Water | 91.9 | Diluent | Formulation for Heavy duty industrial cleaning applications pH ~10.9, Cloud pt = 34 C. |
| Trilon M liquid | 0.5 | Chelator | |
| Potassium Carbonate | 0.6 | Alkaline Builder | |
| Ecosurf SA-7 | 4.0 | Surfactant | |
| Amphoteric 400 | 2 | Surfactant | |
| farnesene dimethyl maleate adduct | 1 | Solvent | |

All-Purpose Cleaner #4

| Ingredient | % | Ingredient Function | Application |
|---|---|---|---|
| Deionized Water | 90.9 | Diluent | Formulation for Heavy duty industrial cleaning applications pH ~10.9, Cloud pt = 45 C. |
| Trilon M liquid | 0.5 | Chelator | |
| Potassium Carbonate | 0.6 | Alkaline Builder | |
| Tergitol 15-S-7 | 4.0 | Surfactant | |
| Alkatrope SXS-40 | 3.0 | Surfactant | |
| farnesene dimethyl maleate adduct | 1 | Solvent | |

All-Purpose Cleaner # 5

| Ingredient | % | Ingredient Function | Application |
|---|---|---|---|
| Deionized Water | 90.2 | Diluent | Formulation for Heavy duty industrial cleaning applications pH ~13-14 Cloud pt = 51 C. |
| Trilon M liquid | 1.0 | Alkaline Buffer | |
| Sodium Metasilicate Pentahydrate | 2.0 | Alkaline Builder | |
| Potassium Hydroxide (45%) | 2.0 | Solvent | |
| Videt Q3 | 4.1 | Surfactant | |
| farnesene dimethyl maleate adduct | 0.75 | Chelator | |

All-Purpose Cleaner Concentrate

| Ingredient | % | Ingredient Function | Application |
|---|---|---|---|
| farnesene dimethyl maleate adduct | 35 | Solvent | Dilutable formulation for light duty industrial cleaning applications |
| Videt ME-80 | 20 | Surfactant | |
| Tomadol 25-7 | 3 | Surfactant | |
| Deionized Water | 42 | Diluent | |

Metal Cleaning Fluid

| Ingredient | % | Ingredient Function | Application |
|---|---|---|---|
| farnesene dimethyl maleate adduct | 90 | Solvent | Metal parts cleaning (e.g. post machining applications) |
| Linear Alcohol (C12-15) Ethoxylate, POE-7 | 10 | Thickener | |

Scrubbing Wipe #1

| Ingredient | % | Ingredient Function | Application |
|---|---|---|---|
| Deionized Water | 91.875 | Diluent | A wipe for tough soil hand and surface cleaning. |
| Stepan BIO-SOFT N1-7 | 2.20 | Surfactant | |
| Eastman Omnia | 2.00 | Solvent | |
| farnesene dimethyl maleate adduct | 1.20 | Solvent | |
| BIO-SOFT EC-639 | 0.88 | Surfactant | |
| AkzoNobel Ethoquad C/25 | 0.73 | Surfactant | |
| Glycerin | 0.50 | Humectant | |
| Stepan Ammonyx LO | 0.18 | Surfactant | |
| Fragrance | 0.15 | Fragrance | |
| Neossance ® Hemisqualane | 0.10 | Emollient | |
| Neossance ® Squalane | 0.10 | Emollient | |
| Acticide MBS | <0.10 | Preservative | |

Scrubbing Wipe #2

| Ingredient | % | Ingredient Function | Application |
|---|---|---|---|
| Pentex 99 (DOSS) | 3.00 | Anionic Emulsifier | A wipe for tough soil hand and surface cleaning. |
| Tergitol 15-S-5 | 2.00 | Non-ionic emulsifier | |
| farnesene dimethyl maleate adduct | 2.75 | Solvent | |
| Deionized Water | 92.10 | Diluent | |
| Acticide SPX | 0.15 | Preservative | |

7.9 Example 9: Industrial or Consumer Product Formulations Comprising Farnesane Dimer The following are various industrial and consumer product formulations comprising farnesane dimer (e.g., Myralene™ 056) as a solvent. Non-limiting examples of industrial and consumer product formulations that comprise farnesane dimer as a solvent include hard surface heavy duty cleaner, pumice hand cleaner, smooth hand cleaner, graffiti remover, solvent degreaser, bug and tar remover, oven cleaner, interior auto cleaner, all-purpose cleaner, metal cleaning fluid, scrubbing wipe, and the like.

Hard Surface Heavy Duty Cleaner

| Ingredient | % | Ingredient Function | Application |
|---|---|---|---|
| Farnesane Dimer | 35 | Solvent | For clean-up of heavy grease surfaces in industrial applications |
| Tomadol 25-7 | 3 | Surfactant | |
| Videt ME-80 | 20 | Surfactant | |
| Deionized Water | 42 | Diluent | |

Pumice Hand Cleaner

| Ingredient | % | Ingredient Function | Application |
|---|---|---|---|
| Farnesane Dimer | 6.14 | Solvent | A waterless hand cleaner containing abrasive for heavy duty cleaning in industrial environments |
| Carbopol Ultrez 10 | 0.3 | Thickener | |
| Deionized Water | 82.81 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Pumice | 4.5 | Abrasive | |

Pumice Hand Cleaner -continued

| Ingredient | % | Ingredient Function | Application |
|---|---|---|---|
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Smooth Hand Cleaner

| Ingredient | % | Ingredient Function | Application |
|---|---|---|---|
| Farnesane Dimer | 6.14 | Solvent | A waterless hand cleaner for heavy duty cleaning in industrial environments |
| Carbopol Ultrez 10 | 0.3 | Thickener | |
| Deionized Water | 87.31 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Graffiti Remover

| Ingredient | % | Ingredient Function | Application |
|---|---|---|---|
| Farnesane Dimer | 18 | Solvent | A cleaner for removing graffiti from painted surfaces |
| Tomadol 25-7 | 0.9 | Surfactant | |
| DBE-LVP | 18 | Solvent | |
| Isopar M | 63.1 | Diluent | |

Solvent Degreaser #1

| Ingredient | % | Ingredient Function | Application |
|---|---|---|---|
| Farnesane Dimer | 9.5 | Solvent | A spray cleaner for removing tars, greases and inks surfaces |
| DBE-LVP | 10 | Solvent | |
| Eastman Omnia Solvent | 3 | Surfactant | |
| Sasol LPA-210 | 77.5 | Diluent | |
| d-Limonene (optional) | Optional 1-2% | Fragrance | |

Solvent Degreaser #2

| Ingredient | % | Ingredient Function | Application |
|---|---|---|---|
| Farnesane Dimer | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional 1-2% | Fragrance | |

Solvent Degreaser #3

| Ingredient | % | Ingredient Function | Application |
|---|---|---|---|
| Farnesane Dimer | 9.5 | Solvent | A biodegradable spray cleaner for removing tars, greases and inks surfaces |
| DBE-LVP | 10 | Solvent | |
| Eastman Omnia Solvent | 3 | Surfactant | |
| KETRUL D 100 | 77.5 | Diluent | |
| d-Limonene (optional) | 1-2% | Optional Fragrance | |

M

Solvent Degreaser #4

| Ingredient | % | Ingredient Function | Application |
|---|---|---|---|
| Farnesane Dimer | 9 | Solvent | A spray cleaner for removing tars, greases and inks surfaces |
| DBE-LVP | 9 | Solvent | |
| Rhodocal IPAM | 0.3 | Surfactant | |
| Isopar M | 81.7 | Diluent | |
| d-Limonene (optional) | 1-2% | Optional Fragrance | |

Solvent Degreaser #5

| Ingredient | % | Ingredient Function | Application |
|---|---|---|---|
| Farnesane Dimer | 9 | Solvent | A biodegradable spray cleaner for removing tars, greases and inks surfaces |
| DBE-LVP | 9 | Solvent | |
| Rhodocal IPAM | 0.3 | Surfactant | |
| HYDROSEAL G 232 H | 81.7 | Diluent | |
| d-Limonene (optional) | 1-2% | Optional Fragrance | |

Solvent Degreaser #6

| Ingredient | % | Ingredient Function | Application |
|---|---|---|---|
| Farnesane Dimer | 9 | Solvent | A biodegradable spray cleaner for removing tars, greases and inks surfaces |
| DBE-LVP | 9 | Solvent | |
| Rhodocal IPAM | 0.3 | Surfactant | |
| KETRUL D 100 | 81.7 | Diluent | |
| d-Limonene (optional) | 1-2% | Optional Fragrance | |

Bug and Tar Remover

| Ingredient | % | Ingredient Function | Application |
|---|---|---|---|
| Farnesane Dimer | 35 | Solvent | Heavy duty external car cleaner for removal of bugs and tar from automotive vehicles |
| Tomadol 25-7 | 3 | Surfactant | |
| Windet ME-80 | 20 | Surfactant | |
| Deionized Water | 42 | Diluent | |

Oven Cleaner

| Ingredient | % | Ingredient Function | Application |
|---|---|---|---|
| Deionized Water | 87.73 | Diluent | Spray cleaner to help remove stains on household ovens |
| Farnesane Dimer | 2 | Solvent | |
| Kelzan ASX-T | 0.35 | Thickener | |
| Sodium Bicarbonate | 2 | Alkaline Buffer | |
| Sodium Metasilicate Pentahydrate | 0.2 | Alkaline Buffer | |
| Trilon M liquid | 0.25 | Chelator | |
| Videt Q3 | 5 | Surfactant | |
| Potassium Hydroxide (45%) | 2.47 | Alkaline Builder | |

Interior Auto Cleaner

| Ingredient | % | Ingredient Function | Application |
|---|---|---|---|
| Deionized Water | 95.5 | Diluent | A spray cleaner for car interior cleaning |
| Sodium Citrate | 1.0 | Alkaline Buffer | |
| Farnesane Dimer | 0.5 | Solvent | |
| AMPHOSOL ® CA | 3.0 | Surfactant | |

All-Purpose Cleaner #1

| Ingredient | % | Ingredient Function | Application |
|---|---|---|---|
| Deionized Water | 91.9 | Diluent | Formulation for Heavy duty industrial cleaning applications pH ~10.9, Cloud pt = 35 C. |
| Trilon M liquid | 0.5 | Chelator | |
| Potassium Carbonate | 0.6 | Alkaline Builder | |
| Tergitol 15-S-7 | 4.0 | Surfactant | |
| Amphoteric 400 | 2 | Surfactant | |
| Farnesane Dimer | 1 | Solvent | |

All-Purpose Cleaner #2

| Ingredient | % | Ingredient Function | Application |
|---|---|---|---|
| Deionized Water | 92.9 | Diluent | Formulation for Heavy duty industrial cleaning applications pH ~10.9, Cloud pt = 40 C. |
| Trilon M liquid | 0.5 | Chelator | |
| Potassium Carbonate | 0.6 | Alkaline Builder | |
| Ecosurf EH-6 | 4.0 | Surfactant | |
| Amphoteric 400 | 1 | Surfactant | |
| Farnesane Dimer | 1 | Solvent | |

All-Purpose Cleaner #3

| Ingredient | % | Ingredient Function | Application |
|---|---|---|---|
| Deionized Water | 91.9 | Diluent | Formulation for Heavy duty industrial cleaning applications pH ~10.9, Cloud pt = 34 C. |
| Trilon M liquid | 0.5 | Chelator | |
| Potassium Carbonate | 0.6 | Alkaline Builder | |
| Ecosurf SA-7 | 4.0 | Surfactant | |
| Amphoteric 400 | 2 | Surfactant | |
| Farnesane Dimer | 1 | Solvent | |

All-Purpose Cleaner #4

| Ingredient | % | Ingredient Function | Application |
|---|---|---|---|
| Deionized Water | 90.9 | Diluent | Formulation for Heavy duty industrial cleaning applications pH ~10.9, Cloud pt = 45 C. |
| Trilon M liquid | 0.5 | Chelator | |
| Potassium Carbonate | 0.6 | Alkaline Builder | |
| Tergitol 15-S-7 | 4.0 | Surfactant | |
| Alkatrope SXS-40 | 3.0 | Surfactant | |
| Farnesane Dimer | 1 | Solvent | |

All-Purpose Cleaner #5

| Ingredient | % | Ingredient Function | Application |
|---|---|---|---|
| Deionized Water | 90.2 | Diluent | Formulation for Heavy duty industrial cleaning applications pH ~13-14 Cloud pt = 51 C. |
| Trilon M liquid | 1.0 | Alkaline Buffer | |
| Sodium Metasilicate Pentahydrate | 2.0 | Alkaline Builder | |
| Potassium Hydroxide (45%) | 2.0 | Solvent | |
| Videt Q3 | 4.1 | Surfactant | |
| Farnesane Dimer | 0.75 | Chelator | |

All-Purpose Cleaner Concentrate

| Ingredient | % | Ingredient Function | Application |
|---|---|---|---|
| Farnesane Dimer | 35 | Solvent | Dilutable formulation for light duty industrial cleaning applications |
| Videt ME-80 | 20 | Surfactant | |
| Tomadol 25-7 | 3 | Surfactant | |
| Deionized Water | 42 | Diluent | |

Metal Cleaning Fluid

| Ingredient | % | Ingredient Function | Application |
|---|---|---|---|
| Farnesane Dimer | 90 | Solvent | Metal parts cleaning (e.g. post machining applications) |
| Linear Alcohol (C12-15) Ethoxylate, POE-7 | 10 | Thickener | |

Scrubbing Wipe #1

| Ingredient | % | Ingredient Function | Application |
|---|---|---|---|
| Deionized Water | 91.875 | Diluent | A wipe for tough soil hand and surface cleaning. |
| Stepan BIO-SOFT N1-7 | 2.20 | Surfactant | |
| Eastman Omnia | 2.00 | Solvent | |
| Farnesane Dimer | 1.20 | Solvent | |
| BIO-SOFT EC-639 | 0.88 | Surfactant | |
| AkzoNobel Ethoquad C/25 | 0.73 | Surfactant | |
| Glycerin | 0.50 | Humectant | |
| Stepan Ammonyx LO | 0.18 | Surfactant | |
| Fragrance | 0.15 | Fragrance | |
| Neossance ® Hemisqualane | 0.10 | Emollient | |
| Neossance ® Squalane | 0.10 | Emollient | |
| Acticide MBS | <0.10 | Preservative | |

Scrubbing Wipe #2

| Ingredient | % | Ingredient Function | Application |
|---|---|---|---|
| Pentex 99 (DOSS) | 3.00 | Anionic Emulsifier | A wipe for tough soil hand and surface cleaning. |
| Tergitol 15-S-5 | 2.00 | Non-ionic emulsifier | |
| Farnesane Dimer | 2.75 | Solvent | |
| Deionized Water | 92.10 | Diluent | |
| Acticide SPX | 0.15 | Preservative | |

7.10 Example 10: Industrial or Consumer Product Formulations Comprising Farnesene Dimer The following are various industrial and consumer product formulations comprising farnesene dimer as a solvent. Non-limiting examples of industrial and consumer product formulations that comprise farnesene dimer (Myralene™ 044) as a solvent include hard surface heavy duty cleaner, pumice hand cleaner, smooth hand cleaner, graffiti remover, solvent degreaser, bug and tar remover, oven cleaner, interior auto cleaner, all-purpose cleaner, metal cleaning fluid, scrubbing wipe, and the like.

Hard Surface Heavy Duty Cleaner

| Ingredient | % | Ingredient Function | Application |
|---|---|---|---|
| farnesene dimer | 35 | Solvent | For clean-up of heavy grease surfaces in industrial applications |
| Tomadol 25-7 | 3 | Surfactant | |
| Videt ME-80 | 20 | Surfactant | |
| Deionized Water | 42 | Diluent | |

Pumice Hand Cleaner

| Ingredient | % | Ingredient Function | Application |
|---|---|---|---|
| farnesene dimer | 6.14 | Solvent | A waterless hand cleaner containing abrasive for heavy duty cleaning in industrial environments |
| Carbopol Ultrez 10 | 0.3 | Thickener | |
| Deionized Water | 82.81 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Pumice | 4.5 | Abrasive | |
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Smooth Hand Cleaner

| Ingredient | % | Ingredient Function | Application |
|---|---|---|---|
| farnesene dimer | 6.14 | Solvent | A waterless hand cleaner for heavy duty cleaning in industrial environments |
| Carbopol Ultrez 10 | 0.3 | Thickener | |
| Deionized Water | 87.31 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Microcare MTO | 0.15 | Preservative | |
| Amyris Squalane | 1 | Emollient | |

Smooth Hand Cleaner

| Ingredient | % | Ingredient Function | Application |
|---|---|---|---|
| Givaduan Fragrance | 0.1 | Fragrance | |
| d-Limonene | 0.95 | Fragrance | |

Graffiti Remover

| Ingredient | % | Ingredient Function | Application |
|---|---|---|---|
| farnesene dimer | 18 | Solvent | A cleaner for removing graffiti from painted surfaces |
| Tomadol 25-7 | 0.9 | Surfactant | |
| DBE-LVP | 18 | Solvent | |
| Isopar M | 63.1 | Diluent | |

Solvent Degreaser #1

| Ingredient | % | Ingredient Function | Application |
|---|---|---|---|
| farnesene dimer | 9.5 | Solvent | A spray cleaner for removing tars, greases and inks surfaces |
| DBE-LVP | 10 | Solvent | |
| Eastman Omnia Solvent | 3 | Surfactant | |
| Sasol LPA-210 | 77.5 | Diluent | |
| d-Limonene (optional) | Optional Fragrance 1-2% | | |

Solvent Degreaser #2

| Ingredient | % | Ingredient Function | Application |
|---|---|---|---|
| farnesene dimer | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional Fragrance 1-2% | | |

Solvent Degreaser #2

| Ingredient | % | Ingredient Function | Application |
|---|---|---|---|
| 0 | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional Fragrance 1-2% | | |

Solvent Degreaser #4

| Ingredient | % | Ingredient Function | Application |
|---|---|---|---|
| farnesene dimer | 9 | Solvent | A spray cleaner for removing tars, greases and inks surfaces |
| DBE-LVP | 9 | Solvent | |
| Rhodocal IPAM | 0.3 | Surfactant | |
| Isopar M | 81.7 | Diluent | |

Solvent Degreaser #4

| Ingredient | % | Ingredient Function | Application |
|---|---|---|---|
| d-Limonene (optional) | Optional Fragrance 1-2% | | |

Solvent Degreaser #5

| Ingredient | % | Ingredient Function | Application |
|---|---|---|---|
| farnesene dimer | 9 | Solvent | A biodegradable spray cleaner for removing tars, greases and inks surfaces |
| DBE-LVP | 9 | Solvent | |
| Rhodocal IPAM | 0.3 | Surfactant | |
| HYDROSEAL G 232 H | 81.7 | Diluent | |
| d-Limonene (optional) | Optional Fragrance 1-2% | | |

Solvent Degreaser #6

| Ingredient | % | Ingredient Function | Application |
|---|---|---|---|
| farnesene dimer | 9 | Solvent | A biodegradable spray cleaner for removing tars, greases and inks surfaces |
| DBE-LVP | 9 | Solvent | |
| Rhodocal IPAM | 0.3 | Surfactant | |
| KETRUL D 100 | 81.7 | Diluent | |
| d-Limonene (optional) | Optional Fragrance 1-2% | | |

Bug and Tar Remover

| Ingredient | % | Ingredient Function | Application |
|---|---|---|---|
| farnesene dimer (e.g., Myralene ™ 044) | 35 | Solvent | Heavy duty external car cleaner for removal of bugs and tar from automotive vehicles |
| Tomadol 25-7 | 3 | Surfactant | |
| Windet ME-80 | 20 | Surfactant | |
| Deionized Water | 42 | Diluent | |

Oven Cleaner

| Ingredient | % | Ingredient Function | Application |
|---|---|---|---|
| Deionized Water | 87.73 | Diluent | Spray cleaner to help remove stains on household ovens |
| Farnesene dimer (e.g., Myralene ™ 044) | 2 | Solvent | |
| Kelzan ASX-T | 0.35 | Thickener | |
| Sodium Biocarbonate | 2 | Alkaline Buffer | |
| Sodium Metasilicate Pentahydrate | 0.2 | Alkaline Buffer | |
| Trilon M liquid | 0.25 | Chelator | |
| Videt Q3 | 5 | Surfactant | |
| Potassium Hydroxide (45%) | 2.47 | Alkaline Builder | |

Interrior Auto Cleaner

| Ingredient | % | Ingredient Function | Application |
|---|---|---|---|
| Deionized Water | 95.5 | Diluent | A spray cleaner for car interior cleaning |
| Sodium Citrate | 1.0 | Alkaline Buffer | |
| farnesene dimer | 0.5 | Solvent | |
| AMPHOSOL ® CA | 3.0 | Surfactant | |

All-Purpose Cleaner #1

| Ingredient | % | Ingredient Function | Application |
|---|---|---|---|
| Deionized Water | 91.9 | Diluent | Formulation for Heavy duty industrial cleaning applications pH ~10.9, Cloud pt = 35 C. |
| Trilon M liquid | 0.5 | Chelator | |
| Potassium Carbonate | 0.6 | Alkaline Builder | |
| Tergitol 15-S-7 | 4.0 | Surfactant | |
| Amphoteric 400 | 2 | Surfactant | |
| farnesene dimer | 1 | Solvent | |

All-Purpose Cleaner #2

| Ingredient | % | Ingredient Function | Application |
|---|---|---|---|
| Deionized Water | 92.9 | Diluent | Formulation for Heavy duty industrial cleaning applications pH ~10.9, Cloud pt = 40 C. |
| Trilon M liquid | 0.5 | Chelator | |
| Potassium Carbonate | 0.6 | Alkaline Builder | |
| Ecosurf EH-6 | 4.0 | Surfactant | |
| Amphoteric 400 | 1 | Surfactant | |
| farnesene dimer | 1 | Solvent | |

All-Purpose Cleaner #3

| Ingredient | % | Ingredient Function | Application |
|---|---|---|---|
| Deionized Water | 91.9 | Diluent | Formulation for Heavy duty industrial cleaning applications pH ~10.9, Cloud pt = 34 C. |
| Trilon M liquid | 0.5 | Chelator | |
| Potassium Carbonate | 0.6 | Alkaline Builder | |
| Ecosurf SA-7 | 4.0 | Surfactant | |
| Amphoteric 400 | 2 | Surfactant | |
| farnesene dimer | 1 | Solvent | |

All-Purpose Cleaner #4

| Ingredient | % | Ingredient Function | Application |
|---|---|---|---|
| Deionized Water | 90.9 | Diluent | Formulation for Heavy duty industrial cleaning applications pH ~10.9, Cloud pt = 45 C. |
| Trilon M liquid | 0.5 | Chelator | |
| Potassium Carbonate | 0.6 | Alkaline Builder | |
| Tergitol 15-S-7 | 4.0 | Surfactant | |
| Alkatrope SXS-40 | 3.0 | Surfactant | |
| farnesene dimer | 1 | Solvent | |

All-Purpose Cleaner #5

| Ingredient | % | Ingredient Function | Application |
|---|---|---|---|
| Deionized Water | 90.2 | Diluent | Formulation for Heavy duty industrial cleaning applications pH ~13-14 Cloud pt = 51 C. |
| Trilon M liquid | 1.0 | Alkaline Buffer | |
| Sodium Metasilicate Pentahydrate | 2.0 | Alkaline Builder | |
| Potassium Hydroxide (45%) | 2.0 | Solvent | |
| Videt Q3 | 4.1 | Surfactant | |
| farnesene dimer | 0.75 | Chelator | |

All-Purpose Cleaner Concentrate

| Ingredient | % | Ingredient Function | Application |
|---|---|---|---|
| farnesene dimer | 35 | Solvent | Dilutable formulation for light duty industrial cleaning applications |
| Videt ME-80 | 20 | Surfactant | |
| Tomadol 25-7 | 3 | Surfactant | |
| Deionized Water | 42 | Diluent | |

Metal Cleaning Fluid

| Ingredient | % | Ingredient Function | Application |
|---|---|---|---|
| farnesene dimer | 90 | Solvent | Metal parts cleaning (e.g. post machining applications) |
| Linear Alcohol (C12-15) Ethoxylate, POE-7 | 10 | Thickener | |

Scrubbing Wipe #1

| Ingredient | % | Ingredient Function | Application |
|---|---|---|---|
| Deionized Water | 91.875 | Diluent | A wipe for tough soil hand and surface cleaning. |
| Stepan BIO-SOFT N1-7 | 2.20 | Surfactant | |
| Eastman Omnia | 2.00 | Solvent | |
| farnesene dimer | 1.20 | Solvent | |
| BIO-SOFT EC-639 | 0.88 | Surfactant | |
| AkzoNobel Ethoquad C/25 | 0.73 | Surfactant | |
| Glycerin | 0.50 | Humectant | |
| Stepan Ammonyx LO | 0.18 | Surfactant | |
| Fragrance | 0.15 | Fragrance | |
| Neossance ® Hemisqualane | 0.10 | Emollient | |
| Neossance ® Squalane | 0.10 | Emollient | |
| Acticide MBS | <0.10 | Preservative | |

Scrubbing Wipe #2

| Ingredient | % | Ingredient Function | Application |
|---|---|---|---|
| Pentex 99 (DOSS) | 3.00 | Anionic Emulsifier | A wipe for tough soil hand and surface cleaning. |
| Tergitol 15-S-5 | 2.00 | Non-ionic emulsifier | |
| farnesene dimer | 2.75 | Solvent | |
| Deionized Water | 92.10 | Diluent | |
| Acticide SPX | 0.15 | Preservative | |

7.11 Example 11: Industrial or Consumer Product Formulations Comprising Farnesane The following are various industrial and consumer product formulations comprising farnesane as a solvent. Non-limiting examples of industrial and consumer product formulations that comprise farnesane (e.g., Myralene™ 40) as a solvent include hard surface heavy duty cleaner, pumice hand cleaner, smooth hand cleaner, graffiti remover, solvent degreaser, bug and tar remover, oven cleaner, interior auto cleaner, all-purpose cleaner, metal cleaning fluid, scrubbing wipe, and the like.

Hard Surface Heavy Duty Cleaner

| Ingredient | % | Ingredient Function | Application |
|---|---|---|---|
| Farnesane | 35 | Solvent | For clean-up of heavy grease surfaces in industrial applications |
| Tomadol 25-7 | 3 | Surfactant | |
| Videt ME-80 | 20 | Surfactant | |
| Deionized Water | 42 | Diluent | |

Pumice Hand Cleaner

| Ingredient | % | Ingredient Function | Application |
|---|---|---|---|
| Farnesane | 6.14 | Solvent | A waterless hand cleaner containing abrasive for heavy duty cleaning in industrial environments |
| Carbopol Ultrez 10 | 0.3 | Thickener | |
| Deionized Water | 82.81 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Pumice | 4.5 | Abrasive | |
| Microcare MTO | 0.15 | Preservative | |
| *Amyris* Squalane | 1 | Emollient | |
| Givaduan Fragrance | 0.1 | Fragrance | |
| d-Limonene | 0.95 | Fragrance | |

Smooth Hand Cleaner

| Ingredient | % | Ingredient Function | Application |
|---|---|---|---|
| Farnesane | 6.14 | Solvent | A waterless hand cleaner for heavy duty cleaning in industrial environments |
| Carbopol Ultrez 10 | 0.3 | Thickener | |
| Deionized Water | 87.31 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Microcare MTO | 0.15 | Preservative | |
| *Amyris* Squalane | 1 | Emollient | |
| Givaduan Fragrance | 0.1 | Fragrance | |
| d-Limonene | 0.95 | Fragrance | |

Graffiti Remover

| Ingredient | % | Ingredient Function | Application |
|---|---|---|---|
| Farnesane | 18 | Solvent | A cleaner for removing graffiti from painted surfaces |
| Tomadol 25-7 | 0.9 | Surfactant | |
| DBE-LVP | 18 | Solvent | |
| Isopar M | 63.1 | Diluent | |

Solvent Degreaser #1

| Ingredient | % | Ingredient Function | Application |
|---|---|---|---|
| Farnesane | 9.5 | Solvent | A spray cleaner for removing tars, greases and inks surfaces |
| DBE-LVP | 10 | Solvent | |
| Eastman Omnia Solvent | 3 | Surfactant | |
| Sasol LPA-210 | 77.5 | Diluent | |
| d-Limonene (optional) | Optional 1-2% | Fragrance | |

Solvent Degreaser #2

| Ingredient | % | Ingredient Function | Application |
|---|---|---|---|
| Farnesane | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional 1-2% | Fragrance | |

Solvent Degreaser #3

| Ingredient | % | Ingredient Function | Application |
|---|---|---|---|
| Farnesane | 9.5 | Solvent | A biodegradable spray cleaner for removing tars, greases and inks surfaces |
| DBE-LVP | 10 | Solvent | |
| Eastman Omnia Solvent | 3 | Surfactant | |
| KETRUL D 100 | 77.5 | Diluent | |
| d-Limonene (optional) | Optional 1-2% | Fragrance | |

Solvent Degreaser #4

| Ingredient | % | Ingredient Function | Application |
|---|---|---|---|
| Farnesane | 9 | Solvent | A spray cleaner for removing tars, greases and inks surfaces |
| DBE-LVP | 9 | Solvent | |
| Rhodocal IPAM | 0.3 | Surfactant | |
| Isopar M | 81.7 | Diluent | |
| d-Limonene (optional) | Optional 1-2% | Fragrance | |

Solvent Degreaser #5

| Ingredient | % | Ingredient Function | Application |
|---|---|---|---|
| Farnesane | 9 | Solvent | A biodegradable spray cleaner for removing tars, greases and inks surfaces |
| DBE-LVP | 9 | Solvent | |
| Rhodocal IPAM | 0.3 | Surfactant | |
| HYDROSEAL G 232 H | 81.7 | Diluent | |
| d-Limonene (optional) | Optional 1-2% | Fragrance | |

Solvent Degreaser #6

| Ingredient | % | Ingredient Function | Application |
|---|---|---|---|
| Farnesane | 9 | Solvent | A biodegradable spray cleaner for removing tars, greases and inks surfaces |
| DBE-LVP | 9 | Solvent | |
| Rhodocal IPAM | 0.3 | Surfactant | |
| KETRUL D 100 | 81.7 | Diluent | |
| d-Limonene (optional) | Optional 1-2% | Fragrance | |

Bug and Tar Remover

| Ingredient | % | Ingredient Function | Application |
|---|---|---|---|
| Farnesane | 35 | Solvent | Heavy duty external car cleaner for removal of bugs and tar from automotive vehicles |
| Tomadol 25-7 | 3 | Surfactant | |
| Windet ME-80 | 20 | Surfactant | |
| Deionized Water | 42 | Diluent | |

Oven Cleaner

| Ingredient | % | Ingredient Function | Application |
|---|---|---|---|
| Deionized Water | 87.73 | Diluent | Spray cleaner to help remove stains on household ovens |
| Farnesane | 2 | Solvent | |
| Kelzan ASX-T | 0.35 | Thickener | |
| Sodium Biocarbonate | 2 | Alkaline Buffer | |
| Sodium Metasilicate Pentahydrate | 0.2 | Alkaline Buffer | |
| Trilon M liquid | 0.25 | Chelator | |
| Videt Q3 | 5 | Surfactant | |
| Potassium Hydroxide (45%) | 2.47 | Alkaline Builder | |

Interior Auto Cleaner

| Ingredient | % | Ingredient Function | Application |
|---|---|---|---|
| Deionized Water | 95.5 | Diluent | A spray cleaner for car interior cleaning |
| Sodium Citrate | 1.0 | Alkaline Buffer | |
| Farnesane | 0.5 | Solvent | |
| AMPHOSOL ® CA | 3.0 | Surfactant | |

All-Purpose Cleaner #1

| Ingredient | % | Ingredient Function | Application |
|---|---|---|---|
| Deionized Water | 91.9 | Diluent | Formulation for Heavy duty industrial cleaning applications pH ~10.9, Cloud pt = 35 C. |
| Trilon M liquid | 0.5 | Chelator | |
| Potassium Carbonate | 0.6 | Alkaline Builder | |
| Tergitol 15-S-7 | 4.0 | Surfactant | |
| Amphoteric 400 | 2 | Surfactant | |
| Farnesane | 1 | Solvent | |

All-Purpose Cleaner #2

| Ingredient | % | Ingredient Function | Application |
|---|---|---|---|
| Deionized Water | 92.9 | Diluent | Formulation for Heavy duty industrial cleaning applications pH ~10.9, Cloud pt = 40 C. |
| Trilon M liquid | 0.5 | Chelator | |
| Potassium Carbonate | 0.6 | Alkaline Builder | |
| Ecosurf EH-6 | 4.0 | Surfactant | |
| Amphoteric 400 | 1 | Surfactant | |
| Farnesane | 1 | Solvent | |

All-Purpose Cleaner #3

| Ingredient | % | Ingredient Function | Application |
|---|---|---|---|
| Deionized Water | 91.9 | Diluent | Formulation for Heavy duty industrial cleaning applications pH ~10.9, Cloud pt = 34 C. |
| Trilon M liquid | 0.5 | Chelator | |
| Potassium Carbonate | 0.6 | Alkaline Builder | |
| Ecosurf SA-7 | 4.0 | Surfactant | |
| Amphoteric 400 | 2 | Surfactant | |
| Farnesane | 1 | Solvent | |

All-Purpose Cleaner #4

| Ingredient | % | Ingredient Function | Application |
|---|---|---|---|
| Deionized Water | 90.9 | Diluent | Formulation for Heavy duty industrial cleaning applications pH ~10.9, Cloud pt = 45 C. |
| Trilon M liquid | 0.5 | Chelator | |
| Potassium Carbonate | 0.6 | Alkaline Builder | |
| Tergitol 15-S-7 | 4.0 | Surfactant | |
| Alkatrope SXS-40 | 3.0 | Surfactant | |
| Farnesane | 1 | Solvent | |

All-Purpose Cleaner # 5

| Ingredient | % | Ingredient Function | Application |
|---|---|---|---|
| Deionized Water | 90.2 | Diluent | Formulation for Heavy duty industrial cleaning applications pH ~13-14 Cloud pt = 51 C. |
| Trilon M liquid | 1.0 | Alkaline Buffer | |
| Sodium Metasilicate Pentahydrate | 2.0 | Alkaline Builder | |
| Potassium Hydroxide (45%) | 2.0 | Solvent | |
| Videt Q3 | 4.1 | Surfactant | |
| Farnesane | 0.75 | Chelator | |

All-Purpose Cleaner Concentrate

| Ingredient | % | Ingredient Function | Application |
|---|---|---|---|
| Farnesane | 35 | Solvent | Dilutable formulation for light duty industrial cleaning applications |
| Videt ME-80 | 20 | Surfactant | |
| Tomadol 25-7 | 3 | Surfactant | |
| Deionized Water | 42 | Diluent | |

Metal Cleaning Fluid

| Ingredient | Ingredient % | Function | Application |
|---|---|---|---|
| Farnesane | 90 | Solvent | Metal parts cleaning (e.g. post machining applications) |
| Linear Alcohol (C12-15) Ethoxylate, POE-7 | 10 | Thickener | |

Scrubbing Wipe #1

| Ingredient | Ingredient % | Function | Application |
|---|---|---|---|
| Deionized Water | 91.875 | Diluent | A wipe for tough soil hand and surface cleaning. |
| Stepan BIO-SOFT N1-7 | 2.20 | Surfactant | |
| Eastman Omnia | 2.00 | Solvent | |
| Farnesane | 1.20 | Solvent | |
| BIO-SOFT EC-639 | 0.88 | Surfactant | |
| AkzoNobel Ethoquad C/25 | 0.73 | Surfactant | |
| Glycerin | 0.50 | Humectant | |
| Stepan Ammonyx LO | 0.18 | Surfactant | |
| Fragrance | 0.15 | Fragrance | |
| Neossance® Hemisqualane | 0.10 | Emollient | |
| Neossance® Squalane | 0.10 | Emollient | |
| Acticide MBS | <0.10 | Preservative | |

Scrubbing Wipe #2

| Ingredient | % | Ingredient Function | Application |
|---|---|---|---|
| Pentex 99 (DOSS) | 3.00 | Anionic Emulsifier | A wipe for tough soil hand and surface cleaning. |
| Tergitol 15-S-5 | 2.00 | Non-ionic emulsifier | |
| Farnesane | 2.75 | Solvent | |
| Deionized Water | 92.10 | Diluent | |
| Acticide SPX | 0.15 | Preservative | |

7.12 Example 12: Industrial or Consumer Product Formulations Comprising Partially Hydrogenated Farnesene (a Mixture of Dihydrofarnesene, Tetrahydrofarnesene and Other $C_{15}$ Hydrocarbons with at Least about 80% Dihydrofarnesene in the Mixture)

The following are various industrial and consumer product formulations comprising partially hydrogenated farnesene (e.g., Myralene™ 10) as a solvent. Non-limiting examples of industrial and consumer product formulations that comprise partially hydrogenated farnesene as a solvent include hard surface heavy duty cleaner, pumice hand cleaner, smooth hand cleaner, graffiti remover, solvent degreaser, bug and tar remover, oven cleaner, interior auto cleaner, all-purpose cleaner, metal cleaning fluid, scrubbing wipe, and the like.

Hard Surface Heavy Duty Cleaner

| Ingredient | % | Ingredient Function | Application |
|---|---|---|---|
| Myralene™ 10 | 35 | Solvent | For clean-up of heavy grease |
| Tomadol 25-7 | 3 | Surfactant | |
| Videt ME-80 | 20 | Surfactant | surfaces in industrial applications |
| Deionized Water | 42 | Diluent | |

Pumice Hand Cleaner

| Ingredient | % | Ingredient Function | Application |
|---|---|---|---|
| Myralene™ 10 | 6.14 | Solvent | A waterless hand cleaner containing abrasive for heavy duty cleaning in industrial environments |
| Carbopol Ultrez 10 | 0.3 | Thickener | |
| Deionized Water | 82.81 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Pumice | 4.5 | Abrasive | |
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Smooth Hand Cleaner

| Ingredient | % | Ingredient Function | Application |
|---|---|---|---|
| Myralene™ 10 | 6.14 | Solvent | A waterless hand cleaner for heavy duty cleaning in industrial environments |
| Carbopol Ultrez 10 | 0.3 | Thickener | |
| Deionized Water | 87.31 | Diluent | |
| Acusol 820 | 1.25 | Surfactant | |
| DBE-LVP | 0.3 | Solvent | |
| Tomadol 25-7 | 1.75 | Surfactant | |
| Triethanolamine (to pH 7.0-7.9) | 0.75 | Neutralizer | |
| Microcare MTO | 0.15 | Preservative | |
| Amyris Squalane | 1 | Emollient | |
| Givaduan Fragrance | 0.1 | Fragrance | |
| d-Limonene | 0.95 | Fragrance | |

Graffiti Remover

| Ingredient | % | Ingredient Function | Application |
|---|---|---|---|
| Myralene™ 10 | 18 | Solvent | A cleaner for removing graffiti from painted surfaces |
| Tomadol 25-7 | 0.9 | Surfactant | |
| DBE-LVP | 18 | Solvent | |
| Isopar M | 63.1 | Diluent | |

Solvent Degreaser #1

| Ingredient | % | Ingredient Function | Application |
|---|---|---|---|
| Myralene™ 10 | 9.5 | Solvent | A spray cleaner for removing tars, greases and inks surfaces |
| DBE-LVP | 10 | Solvent | |
| Eastman Omnia Solvent | 3 | Surfactant | |
| Sasol LPA-210 | 77.5 | Diluent | |
| d-Limonene (optional) | Optional 1-2% | Fragrance | |

Solvent Degreaser #2

| Ingredient | % | Ingredient Function | Application |
|---|---|---|---|
| Myralene ™ 10 | 9.5 | Solvent | A biodegradable spray cleaner for removing tars, greases and inks surfaces |
| DBE-LVP | 10 | Solvent | |
| Eastman Omnia Solvent | 3 | Surfactant | |
| HYDROSEAL G 232 H | 77.5 | Diluent | |
| d-Limonene (optional) | Optional 1-2% | Fragrance | |

Solvent Degreaser #3

| Ingredient | % | Ingredient Function | Application |
|---|---|---|---|
| Myralene ™ 10 | 9.5 | Solvent | A biodegradable spray cleaner for removing tars, greases and inks surfaces |
| DBE-LVP | 10 | Solvent | |
| Eastman Omnia Solvent | 3 | Surfactant | |
| KETRUL D 100 | 77.5 | Diluent | |
| d-Limonene (optional) | Optional 1-2% | Fragrance | |

Solvent Degreaser #4

| Ingredient | % | Ingredient Function | Application |
|---|---|---|---|
| Myralene ™ 10 | 9 | Solvent | A spray cleaner for removing tars, greases and inks surfaces |
| DBE-LVP | 9 | Solvent | |
| Rhodocal IPAM | 0.3 | Surfactant | |
| Isopar M | 81.7 | Diluent | |
| d-Limonene (optional) | Optional 1-2% | Fragrance | |

Solvent Degreaser #5

| Ingredient | % | Ingredient Function | Application |
|---|---|---|---|
| Myralene ™ 10 | 9 | Solvent | A biodegradable spray cleaner for removing tars, greases and inks surfaces |
| DBE-LVP | 9 | Solvent | |
| Rhodocal IPAM | 0.3 | Surfactant | |
| HYDROSEAL G 232 H | 81.7 | Diluent | |
| d-Limonene (optional) | Optional 1-2% | Fragrance | |

Solvent Degreaser #6

| Ingredient | % | Ingredient Function | Application |
|---|---|---|---|
| Myralene ™ 10 | 9 | Solvent | A biodegradable spray cleaner for removing tars, greases and inks surfaces |
| DBE-LVP | 9 | Solvent | |
| Rhodocal IPAM | 0.3 | Surfactant | |
| KETRUL D 100 | 81.7 | Diluent | |
| d-Limonene (optional) | Optional 1-2% | Fragrance | |

Bug and Tar Remover

| Ingredient | % | Ingredient Function | Application |
|---|---|---|---|
| Myralene ™ 10 | 35 | Solvent | Heavy duty external car cleaner for removal of bugs and tar from automotive vehicles |
| Tomadol 25-7 | 3 | Surfactant | |
| Windet ME-80 | 20 | Surfactant | |
| Deionized Water | 42 | Diluent | |

Oven Cleaner

| Ingredient | % | Ingredient Function | Application |
|---|---|---|---|
| Deionized Water | 87.73 | Diluent | Spray cleaner to help remove stains on household ovens |
| Myralene ™ 10 | 2 | Solvent | |
| Kelzan ASX-T | 0.35 | Thickener | |
| Sodium Biocarbonate | 2 | Alkaline Buffer | |
| Sodium Metasilicate Pentahydrate | 0.2 | Alkaline Buffer | |
| Trilon M liquid | 0.25 | Chelator | |
| Videt Q3 | 5 | Surfactant | |
| Potassium Hydroxide (45%) | 2.47 | Alkaline Builder | |

Interior Auto Cleaner

| Ingredient | % | Ingredient Function | Application |
|---|---|---|---|
| Deionized Water | 95.5 | Diluent | A spray cleaner for car interior cleaning |
| Sodium Citrate | 1.0 | Alkaline Buffer | |
| Myralene ™ 10 | 0.5 | Solvent | |
| AMPHOSOL ® CA | 3.0 | Surfactant | |

All-Purpose Cleaner #1

| Ingredient | % | Ingredient Function | Application |
|---|---|---|---|
| Deionized Water | 91.9 | Diluent | Formulation for Heavy duty industrial cleaning applications pH ~10.9, Cloud pt = 35 C. |
| Trilon M liquid | 0.5 | Chelator | |
| Potassium Carbonate | 0.6 | Alkaline Builder | |
| Tergitol 15-S-7 | 4.0 | Surfactant | |
| Amphoteric 400 | 2 | Surfactant | |
| Myralene ™ 10 | 1 | Solvent | |

All-Purpose Cleaner #2

| Ingredient | % | Ingredient Function | Application |
|---|---|---|---|
| Deionized Water | 92.9 | Diluent | Formulation for Heavy duty industrial cleaning applications pH ~10.9, Cloud pt = 40 C. |
| Trilon M liquid | 0.5 | Chelator | |
| Potassium Carbonate | 0.6 | Alkaline Builder | |
| Ecosurf EH-6 | 4.0 | Surfactant | |
| Amphoteric 400 | 1 | Surfactant | |
| Myralene ™ 10 | 1 | Solvent | |

| All-Purpose Cleaner #3 | | | |
|---|---|---|---|
| Ingredient | % | Ingredient Function | Application |
| Deionized Water | 91.9 | Diluent | Formulation for Heavy duty industrial cleaning applications pH ~10.9, Cloud pt = 34 C. |
| Trilon M liquid | 0.5 | Chelator | |
| Potassium Carbonate | 0.6 | Alkaline Builder | |
| Ecosurf SA-7 | 4.0 | Surfactant | |
| Amphoteric 400 | 2 | Surfactant | |
| Myralene ™ 10 | 1 | Solvent | |

| All-Purpose Cleaner #4 | | | |
|---|---|---|---|
| Ingredient | % | Ingredient Function | Application |
| Deionized Water | 90.9 | Diluent | Formulation for Heavy duty industrial cleaning applications pH ~10.9, Cloud pt = 45 C. |
| Trilon M liquid | 0.5 | Chelator | |
| Potassium Carbonate | 0.6 | Alkaline Builder | |
| Tergitol 15-S-7 | 4.0 | Surfactant | |
| Alkatrope SXS-40 | 3.0 | Surfactant | |
| Myralene ™ 10 | 1 | Solvent | |

| All-Purpose Cleaner # 5 | | | |
|---|---|---|---|
| Ingredient | % | Ingredient Function | Application |
| Deionized Water | 90.2 | Diluent | Formulation for Heavy duty industrial cleaning applications pH ~13-14 Cloud pt = 51 C. |
| Trilon M liquid | 1.0 | Alkaline Buffer | |
| Sodium Metasilicate Pentahydrate | 2.0 | Alkaline Builder | |
| Potassium Hydroxide (45%) | 2.0 | Solvent | |
| Videt Q3 | 4.1 | Surfactant | |
| Myralene ™ 10 | 0.75 | Chelator | |

| All-Purpose Cleaner Concentrate | | | |
|---|---|---|---|
| Ingredient | % | Ingredient Function | Application |
| Myralene ™ 10 | 35 | Solvent | Dilutable formulation for light duty industrial cleaning applications |
| Videt ME-80 | 20 | Surfactant | |
| Tomadol 25-7 | 3 | Surfactant | |
| Deionized Water | 42 | Diluent | |

| Metal Cleaning Fluid | | | |
|---|---|---|---|
| Ingredient | % | Ingredient Function | Application |
| Myralene ™ 10 | 90 | Solvent | Metal parts cleaning (e.g. post machining applications) |
| Linear Alcohol (C12-15) Ethoxylate, POE-7 | 10 | Thickener | |

| Scrubbing Wipe #1 | | | |
|---|---|---|---|
| Ingredient | % | Ingredient Function | Application |
| Deionized Water | 91.875 | Diluent | A wipe for tough soil hand and surface cleaning. |
| Stepan BIO-SOFT N1-7 | 2.20 | Surfactant | |
| Eastman Omnia | 2.00 | Solvent | |
| Myralene ™ 10 | 1.20 | Solvent | |
| BIO-SOFT EC-639 | 0.88 | Surfactant | |
| AkzoNobel Ethoquad C/25 | 0.73 | Surfactant | |
| Glycerin | 0.50 | Humectant | |
| Stepan Ammonyx LO | 0.18 | Surfactant | |
| Fragrance | 0.15 | Fragrance | |
| Neossance ® Hemisqualane | 0.10 | Emollient | |
| Neossance ® Squalane | 0.10 | Emollient | |
| Acticide MBS | <0.10 | Preservative | |

| Scrubbing Wipe #2 | | | |
|---|---|---|---|
| Ingredient | % | Ingredient Function | Application |
| Pentex 99 (DOSS) | 3.00 | Anionic Emulsifier | A wipe for tough soil hand and surface cleaning. |
| Tergitol 15-S-5 | 2.00 | Non-ionic emulsifier | |
| Myralene ™ 10 | 2.75 | Solvent | |
| Deionized Water | 92.10 | Diluent | |
| Acticide SPX | 0.15 | Preservative | |

7.13 Example 13: Spreadability/Viscosity of Compounds Derived from Bio-Based Farnesene This example provides spreadability and kinematic viscosity of several compounds derived from bio-based farnesene. Viscosity was measured using ASTM D7042, a standard test method for dynamic viscosity and density of liquids by Stabinger Viscometer (and the calculation of kinematic viscosity). Measurements were performed at 20° C. Spreadability was measured using test method APPO9 as described in www.floratech.com.

The results are shown the table below and graphically illustrated in FIG. 1.

| Code Name | Spreadability ($mm^2$/10 min) | Kinematic Viscosity at 20° C. (cSt) | Chemical Information | Origin |
|---|---|---|---|---|
| AMY-1 | 18,150 | 2.60 | C15 hydrocarbon, partially hydrogenated | Derived from plant sugar (all except some hydrogens) |
| AMY-2 | 5,629 | 113.03 | C30, hydrocarbon, fully saturated | Derived from plant sugar (all except some hydrogens) |
| AMY-3 | 6,779 | 65.88 | Olefinic diester, terpene hydrocarbons | Semi natural, semi synthetic |
| Neossance Hemisqualane | 16,700 | 3.54 | C15 hydrocarbon, fully hydrogenated | Derived from plant sugar (all exept some hydrogens) |
| Neossance Squalane | 8,900 | 42.00 | C30, hydrocarbon, fully saturated | Derived from plant sugar (all exept some hydrogens) |

As illustrated in FIG. 1 and the above table, spreadability and viscosity of compounds derived from bio-based farnesene (i.e., farnesane, squalane, partially hydrogenated farnesene (AMY-1=Myralene 10), farnesane dimer (AMY-2), and farnesene dimethyl maleate adduct (AMY-3) have good spreadability and viscosity properties. These compounds derived from bio-based farnesene are good substitutes for petroleum based non-polar emollients.

One or more features from any embodiments described herein may be combined with one or more features of any other embodiment described herein without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A personal care product composition comprising
one or more $C_{15}$ hydrocarbon compounds derived from bio-based farnesene, one or more farnesene dimers derived from bio-based farnesene, one or more farnesane dimers derived from bio-based farnesene, farnesene dimethyl maleate adduct, or a combination thereof,
and
one or more additional components,
wherein the one or more additional components are not farnesene, farnesene derivatives, reactants or reaction products produced by catalytic reactions of farnesene, or reactants or reaction products produced by hydrogenation of farnesene,
and
the personal care product composition optionally comprising bio-based farnesene,
wherein the total amount of farnesene and farnesene derivatives in the composition comprises 0.1 wt. % to 99.9 wt. % of the personal care product composition,
and
wherein the personal care product composition is formulated to be applied to skin, hair or nails.

2. The personal care product composition of claim 1, wherein the personal care product composition comprises dihydrofarnesene as one of the one or more $C_{15}$ hydrocarbon compounds derived from bio-based farnesene.

3. The personal care product composition of claim 2, wherein the one or more $C_{15}$ hydrocarbon compounds further comprise tetrahydrofarnesene.

4. The personal care product composition of claim 3, wherein the one or more $C_{15}$ hydrocarbon compounds derived from the bio-based farnesene comprise about 78 wt. % to about 97 wt. % dihydrofarnesene and about 2 wt. % to about 20 wt. % tetrahydrofarnesene, compared to a total amount of farnesene and farnesene derivatives in the composition.

5. The personal care product composition of claim 1, wherein the personal care product composition comprises farnesane.

6. The personal care product composition of claim 1, wherein the personal care product composition further comprises squalane and isosqualane, wherein the proportion of squalane to isosqualane, by weight, is between about 2:1 to about 25:1.

7. The personal care product composition of claim 1, wherein the personal care product composition comprises one or more farnesene dimers or one or more farnesane dimers.

8. The personal care product composition of claim 1, wherein the personal care product composition comprises farnesene dimethyl maleate adduct.

9. A personal care product composition comprising
one or more $C_{15}$ hydrocarbon compounds derived from bio-based farnesene, one or more farnesene dimers derived from bio-based farnesene, one or more farnesane dimers derived from bio-based farnesene, farnesene dimethyl maleate adduct, or a combination thereof,
and the personal care product composition optionally comprising bio-based farnesene,
wherein the personal care product composition further comprises water, emulsifier, emollient, flavor, fragrance, essential oil, or a combination thereof,
and
wherein the total amount of farnesene and farnesene derivatives in the composition comprise 0.1 wt. % to 99.9 wt. % of the personal care product composition.

10. A personal care product comprising the personal care product composition of claim 9, wherein the personal care product composition is formulated as a hair care product, lip care product, skin care product, hygiene product, body care product, cosmetic makeup, or sun care product.

11. The personal care product of claim 10, wherein the personal care product is a shampoo, conditioner, anti-frizz treatment, hair repair serum, lip gloss, lip balm, face serum, face cream, night cream, eye serum, eye cream, moisturizer, makeup remover, face cleanser, sanitizing lotion, body lotion, after shave lotion, or sun block lotion.

12. A method of using the personal care product composition of claim 1, the method comprising applying the personal care product composition to skin, hair or nails.

13. An industrial or consumer product composition comprising bio-based farnesene, one or more hydrocarbon compounds derived from the bio-based farnesene, farnesene dimethyl maleate adduct, or a combination thereof,
wherein the industrial or consumer product composition is formulated to be applied to a substrate for degreasing, and is formulated for a product other than a personal care product,
wherein the one or more hydrocarbon compounds comprise dihydrofarnesene,
and
wherein the total amount of farnesene and farnesene derivatives in the composition comprise 0.1 wt. % to 99.9 wt. % of the industrial or consumer product composition.

14. The industrial or consumer product composition of claim 13, wherein the one or more hydrocarbon compounds further comprise tetrahydrofarnesene.

15. The industrial or consumer product composition of claim 14, wherein the industrial or consumer product composition comprises the one or more hydrocarbon compounds derived from the bio-based farnesene comprising about 78 wt. % to about 97 wt. % dihydrofarnesene and about 2 wt. % to about 20 wt. % tetrahydrofarnesene, compared to a total amount of farnesene and farnesene derivatives in the composition.

16. The industrial or consumer product composition of claim 13, wherein the industrial or consumer product composition comprises farnesene dimethyl maleate adduct.

17. The industrial or consumer product composition of claim 13, wherein the industrial or consumer product composition further comprises water, emulsifier, emollient, flavor, fragrance, essential oil, or a combination thereof.

18. The industrial or consumer product of claim 13, wherein the industrial or consumer product is an engine degreaser.

19. A method of using the industrial or consumer product composition of claim 13, the method comprising applying the industrial or consumer product composition to the substrate to degrease the substrate.

20. The personal care product composition of claim 1, wherein the one or more $C_{15}$ hydrocarbon compounds derived from bio-based farnesene, the one or more farnesene dimers derived from bio-based farnesene, and/or the one or more farnesane dimers derived from bio-based farnesene are produced from bio-based farnesene by catalytic reaction, chemical reaction, thermal reaction, hydrogenation, or any combination thereof.

21. The personal care product composition of claim 9, wherein the one or more $C_{15}$ hydrocarbon compounds derived from bio-based farnesene, the one or more farnesene dimers derived from bio-based farnesene, and/or the one or more farnesane dimers derived from bio-based farnesene are produced from bio-based farnesene by catalytic reaction, chemical reaction, thermal reaction, hydrogenation, or any combination thereof.

22. The industrial or consumer product composition of claim 13, wherein the one or more hydrocarbon compounds derived from the bio-based farnesene are produced from bio-based farnesene by catalytic reaction, chemical reaction, thermal reaction, hydrogenation, or any combination thereof.

23. The industrial or consumer product of claim 13, wherein the product comprises at least 80 wt. % water.

* * * * *